United States Patent [19]
Radesca et al.

[11] Patent Number: 5,530,124
[45] Date of Patent: Jun. 25, 1996

[54] METHOD FOR PREPARING CYCLIC UREAS AND THEIR USE FOR THE SYNTHESIS OF HIV PROTEASE INHIBITORS

[75] Inventors: Lilian A. Radesca, Newark; Gregory D. Harris, Wilmington; Edward K. W. Wat, Wilmington; Robert E. Waltermire, Wimington, all of Del.

[73] Assignee: The DuPont Merck Pharmaceutical Company, Wilmington, Del.

[21] Appl. No.: 269,320

[22] Filed: Jun. 30, 1994

[51] Int. Cl.$^6$ .................. C07D 491/056; C07C 221/00
[52] U.S. Cl. ............................ 540/503; 564/502
[58] Field of Search ............................. 540/503; 564/502

[56] References Cited

U.S. PATENT DOCUMENTS 5,294,720  3/1994  Jadhav et al. ................ 546/265

FOREIGN PATENT DOCUMENTS 2026832   3/1991   Canada.
402646    5/1990   European Pat. Off..
WO9307128 10/1991  WIPO.
WO93/23361 5/1993  WIPO.

OTHER PUBLICATIONS

Leanna, M. R. et al. *Tetrahed. Lett.* 35, 5029–5032 (1992).
Anelli, P. L. et al. *J. Org. Chem.* 52, 2559–2562 (1987).
Gordon, A. J. et al. *The Chemist's Companion. A Handbook of Practical Data, Techniques and References.* (Wiley & Sons, New York), p. 442 (1972).
Katritzky, A. R. *Handbook of Heterocyclic Chemistry* (Pergamon Press, Oxford), pp. 148, 151, 167, 169, 313, 315, 316 and 324. (1985).
Keana, J. F. W. *Chem. Rev.* 78, 37 (1978).
Konradi, A. W. et al. *J. Org. Chem.* 57, 28–32 (1992).
Anelli, P. L. et al. Org. Syn. 69, 212–219 (1990).
D. K. Kempf, et al., *J. Org. Chem.* 57, 5692. (1992) Publication month not provided.

Mash et al. *Org. Synthesis* 68 92 (1989) Publication month not provided.
W. R. Baker and S. L. Condon, J. Org. Chem., 1993, 58, 3277–3284. Publication month not provided.
Dreyer et al., Biochemistry, 1993, 32, 937–947 Publication month not provided.
Lam et al., Science, 1994, 263, 380–384. (Jan.).
B. Chenera, J. C. Boehm & G. B. Dreyer, Bioorganic & Med. Chem. Lett., 1991, 1, 219–222. Publication month not provided.
P. K. Jadhav & F. J. Woerner, Bioorganic & Med. Chem. Lett., 1992, 2, 353–356. Publication month not provided.
A. K. Ghosh, S. P. McKee & W. J. Thompson, Tetrahedron Lett., 1991, 32, 5729–5732. Publication month not provided.

*Primary Examiner*—Cecilia Tsang
*Assistant Examiner*—King Lit Wong

[57] ABSTRACT

This invention provides improved synthetic processes for the preparation of hydroxy-protected cyclic urea compounds of Formula (IX),

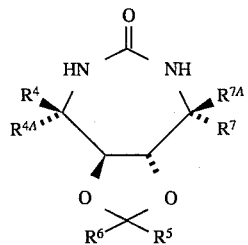

which are useful as intermediates for the preparation of cyclic urea human immunodeficiency virus (HIV) protease inhibitors, from N-protected aminoaldehydes. The processes of the present invention provide high yields, can be conducted on multikilogram scale, and eliminate the need for chromatographic purification of intermediates or final product.

20 Claims, No Drawings

METHOD FOR PREPARING CYCLIC UREAS AND THEIR USE FOR THE SYNTHESIS OF HIV PROTEASE INHIBITORS

FIELD OF THE INVENTION

The present invention relates generally to processes for the preparation of cyclic urea compounds and derivatives thereof and intermediates for the synthesis of cyclic urea compounds, such cyclic urea compounds being useful as inhibitors of human immunodeficiency virus (HIV) protease.

BACKGROUND OF THE INVENTION

Several methods for the oxidation of α-amino alcohols to α-amino aldehydes are known in the art: 1) dimethylsulfoxide (DMSO)/oxalyl chloride; 2) DMSO/trifluoroacetic anhydride; 3) DMSO/sulfur trioxide; and 4) DMSO/dicyclohexylcarbodiimide. These methods are variants of the well known Swern oxidation reaction.

Leanna et al., Tetrahedron Letters 33 (5), 5029-32 (1992), disclose an oxidation process using 2,2,6,6-tetramethyl-1-piperidinyloxy free radical (TEMPO) for the preparation of Cbz-L-phenylalaninal from Cbz-L-phenylalaninol using ethyl acetate/toluene mixtures or dichloromethane as reaction solvent, 0.35M sodium hypochlorite solution, and the use of stoichiometric sodium bromide.

Complexation of vanadium(III) chloride with tetrahydrofuran (THF) is described in the literature (see Cotton et al., *Inorg. Chem.* (1985) 24, 913). Reduction of the complex with zinc to form Caulton's reagent:

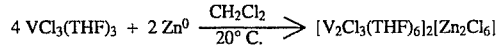

and coupling of Cbz-L-phenylalaninal to form (2S, 3R, 4R, 5S) -diol:

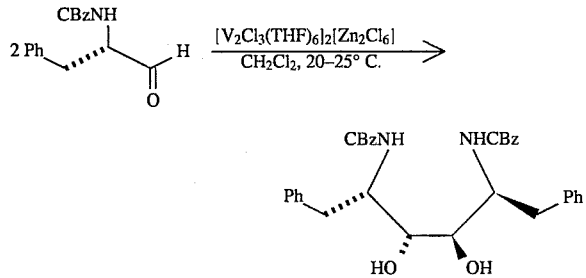

is disclosed by Kempf et al., J. Org. Chem. 57, 5692 (1992) Kempf et al. describe a lengthy procedure for isolating and purifying the indicated diol diastereomer from the mixture of isomers produced in the reaction.

The following references disclose the preparation of noncyclic diaminediol compounds as HIV protease inhibitors: Dreyer et al., *Biochemistry* 32 (3), 937-47 (1993); Canadian Patent Application 2,026,832 (German Patent Application DE 4030350); European Patent Application No. WO 92/00948; European Patent Application Publication Number 402,646; U.S. Pat. No. 4,837,204; European Patent Application Publication Number 486,948; PCT International Publication Number WO 93/23,361.

The preparation of noncyclic diaminediol compounds as HIV protease inhibitors is also disclosed in Jadhav et al., U.S. Pat. No. 5,294,720.

Lam et al., PCT International Publication Number WO 93/07,128 discloses cyclic carbonyl compounds and derivatives thereof which are useful as human immunodeficiency virus (HIV) protease inhibitors for the treatment of HIV infection. The compounds disclosed in WO 93/07128 include cyclic HIV protease inhibitor compounds of the formula below where W may be —N($R^{22}$)C(=O)N($R^{23}$)—.

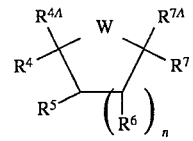

Copending commonly assigned U.S. patent application Ser. No. 08/197,630, filed Feb. 16, 1994 also discloses cyclic HIV protease inhibitors, including cyclic urea HIV protease inhibitors, of the formula below wherein W may be —N($R^{22}$)C(=O)N($R^{23}$)—.

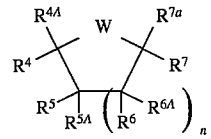

As disclosed in Lam et al., PCT International Publication Number WO 93/07,128 and copending commonly assigned U.S. patent application Ser. No. 08/197,630, such cyclic sulfamide compounds, which may be made using the processes of the present invention, are non-peptidic, low molecular weight, orally bioavailable compounds useful as inhibitors of HIV protease and for the treatment of HIV infection. There is, therefore, a need for more efficient and cost-effective methods for the preparation of such cyclic urea HIV protease inhibitor compounds in high yields from readily available starting materials. The present invention provides improved processes for the synthesis of such cyclic urea HIV protease inhibitor compounds and processes for the synthesis of intermediates for the synthesis of such cyclic urea HIV protease inhibitor compounds.

SUMMARY OF THE INVENTION

This invention provides improved synthetic processes for the preparation of hydroxy-protected cyclic urea compounds, useful as intermediates for the preparation of cyclic urea human immunodeficiency virus (HIV) protease inhibitors, from N-protected aminoaldehydes. The processes of the present invention provide high yields, can be conducted on a multikilogram scale, and eliminate the need for chromatographic purification of intermediates or the desired final product.

There is provided by this invention a process for the preparation of compounds of formula (IX):

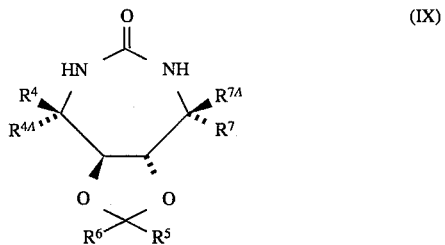

wherein $R^4$, $R^{4A}$, $R^{7A}$, $R^7$, $R^5$ and $R^6$ are defined below, said process comprising one of more of the following steps:

(1) (oxidation) reacting a compound of formula (I):

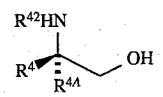
(I)

wherein $R^{42}$ is an amine protecting group defined below, with 2,2,6,6-tetramethyl-1-piperidinyloxy free radical (TEMPO) or other suitable TEMPO-like reagent, sodium hypochlorite, and sodium bromide in water and a suitable aprotic solvent, to form a compound of formula (II):

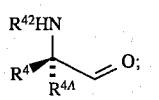
(II)

(2) (coupling) reacting a compound of formula (III):

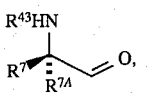
(III)

wherein $R^{43}$ is an amine protecting group as defined below, with a compound of formula (II) and Caulton's reagent in a suitable aprotic solvent, to form a compound of formula (IV):

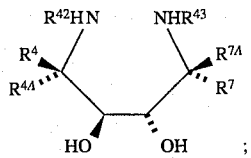
(IV)

(3) (hydroxyl protection) contacting a compound of formula (IV) with a suitable hydroxy protecting group reagent (preferably a suitable halogen activated triethylsilyl (TES) hydroxy protecting group reagent, in the presence of a base), to form a compound of formula (V):

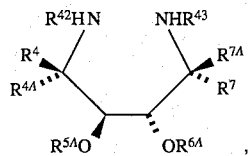
(V)

where $R^{5A}$ and $R^{6A}$ are hydroxy protecting groups (preferably TES), said $R^{5A}$ and $R^{6A}$ hydroxy protecting groups not being removed under a condition or reagent, or combination thereof, to effect the removal of the amine protecting groups $R^{42}$ and $R^{43}$ according to step (4);

(4) (nitrogen deprotection) contacting a compound of formula (V) with a reagent or condition, or combination thereof, to effect the removal of the amine protecting groups $R^{42}$ and $R^{43}$ without removal of the $R^{5A}$ and $R^{6A}$ hydroxy protecting groups, to form a compound of formula (VI):

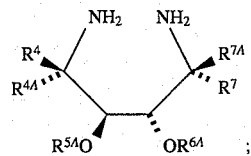
(VI)

(5) (cyclization) contacting a compound of formula (VI) with a suitable cyclizing reagent, to form a compound of formula (VII):

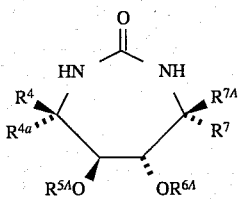
(VII)

(6) (hydroxyl deprotection) contacting a compound of formula (VII) with a reagent or conditions, or combination thereof, to effect the removal of the $R^{5A}$ and $R^{6A}$ hydroxy protecting groups, in a suitable solvent, to form a compound of formula (VIII):

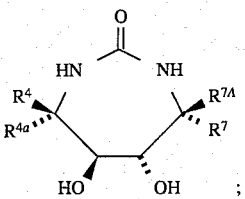
(VIII)

(7) (hydroxyl protection with cyclic ketal) contacting a compound of formula (VIII) with a suitable cyclic acetal hydroxyl protecting group reagent, to obtain a compound of formula (IX).

DETAILED DESCRIPTION OF THE INVENTION

The present invention provides methods for the preparation of cyclic acetal protected cyclic urea compounds of formula (IX) and derivatives thereof. Such compounds of formula (IX) are useful as intermediates for the preparation of cyclic urea HIV protease inhibitor compounds.

There is provided by this invention a process for the preparation of compounds of formula (IX):

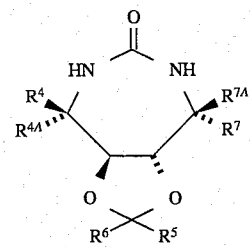
(IX)

wherein $R^4$, $R^{4A}$, $R^{7A}$, $R^7$, $R^5$ and $R^6$ are defined below, said process comprising one of more of the following steps:

(1) (oxidation) reacting a compound of formula (I):

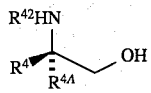
(I)

wherein $R^{42}$ is an amine protecting group defined below, with 2,2,6,6-tetramethyl-1-piperidinyloxy free radical (TEMPO) or other TEMPO-like free radical reagent, sodium hypochlorite, and sodium bromide in water and a suitable aprotic solvent, to form a compound of formula (II):

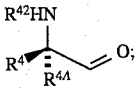
(II)

(2) (coupling) reacting a compound of formula (III):

wherein $R^{43}$ is an amine protecting group as defined below, with a compound of formula (II) and Caulton's reagent in a suitable aprotic solvent, to form a compound of formula (IV):

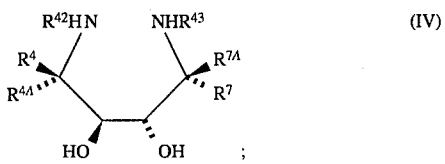

(3) (hydroxyl protection) contacting a compound of formula (IV) with a suitable hydroxy protecting group reagent (preferably a suitable halogen activated triethylsilyl (TES) hydroxy protecting group reagent, in the presence of a base), to form a compound of formula (V):

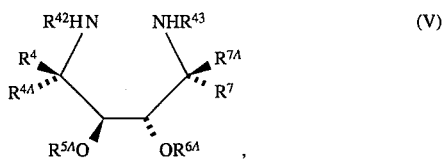

where $R^{5A}$ and $R^{6A}$ are hydroxy protecting groups (preferably TES), said $R^{5A}$ and $R^{6A}$ hydroxy protecting groups not being removed in the presence of a reagent or conditions, or combination thereof, effective to remove the amine protecting groups $R^{42}$ and $R^{43}$ according to step (4);

(4) (nitrogen deprotection) contacting a compound of formula (V) with a reagent or conditions, or combination thereof, to effect the removal of the amine protecting groups $R^{42}$ and $R^{43}$, without removal of the $R^{5A}$ and $R^{6A}$ hydroxy protecting groups, to form a compound of formula (VI):

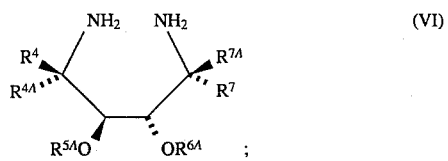

(5) (cyclization) contacting a compound of formula (VI) with a suitable cyclizing reagent, to form a compound of formula (VII):

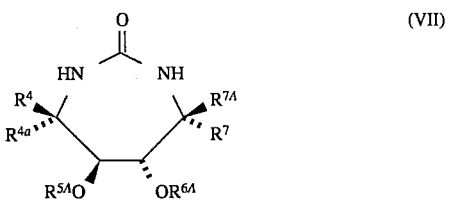

(6) (hydroxyl deprotection) contacting a compound of formula (VII) with a reagent or conditions, or combination thereof, to effect the removal of the $R^{5A}$ and $R^{6A}$ hydroxy protecting groups, in a suitable solvent, to form a compound of formula (VIII):

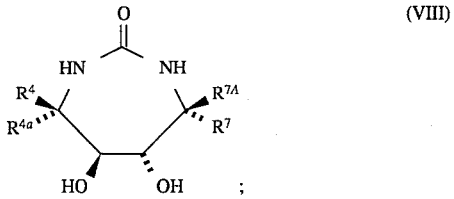

(7) (hydroxyl protection with cyclic ketal) contacting a compound of formula (VIII) with a suitable cyclic acetal hydroxyl protecting group reagent (preferably a cyclic acetal hydroxyl protecting group reagent of formula:

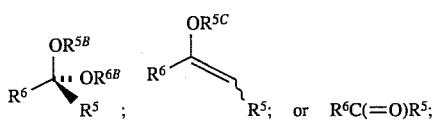

wherein $R^5$, $R^6$, $R^{5B}$, $R^{6B}$ and $R^{5c}$ are defined below), and a suitable catalyst, to obtain a compound of formula (IX).

The present invention provides a process for the preparation of compounds of formula (IX):

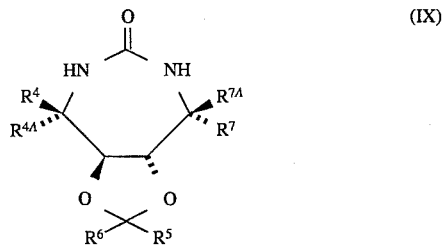

wherein:

$R^4$ and $R^7$ are independently selected from the following groups:
hydrogen;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
a $C_3$–$C_{14}$ carbocyclic ring system substituted with 0–3 $R^{11}$ or 0–3 $R^{12}$;
a 5- to 10-membered heterocyclic ring system containing 1 to 4 heteroatoms independently selected from oxygen, nitrogen or sulfur, said heterocyclic ring system being substituted with 0–2 $R^{12}$;
—$OR^{13}$; —$SR^{13}$; $CO_2R^{13}$;

$R^{4A}$ and $R^{7A}$ are independently selected from the following groups:
hydrogen;
$C_1$–$C_4$ alkyl substituted with 0–6 chloro or fluoro or 0–3 $C_1$–$C_2$ alkoxy;
benzyl substituted with 0–6 chloro or fluoro or 0–3 $C_1$–$C_2$ alkoxy;
—$OR^{13}$; —$SR_{13}$; $CO_2R_{13}$;

$R^4$ and $R^{4A}$ can alternatively join to form a 5–7 membered carbocyclic ring substituted with 0–2 $R^{12}$;

$R^7$ and $R^{7A}$ can alternatively join to form a 5–7 membered carbocyclic ring substituted with 0–2 $R^{12}$;

$R^5$ and $R^6$ are independently H, $C_1$–$C_4$ alkyl, $C_1$–$C_4$ alkoxy, $C_6$–$C_{10}$ aryl, $C_7$–$C_{14}$ arylalkyl, $C_3$–$C_7$ cycloalkyl, or, alternately, $R^1$ and $R^2$ can be taken together with the carbon to which they are attached to form a 3–7 membered saturated carbocyclic ring system or can be taken together to be keto;

$R^{11}$ is selected from one or more of the following:

H chloro, fluoro, cyano, —$CH_2NR^{13}R^{14}$—$NR^{13}R^{14}$, —$CO_2R^{13}$, —$OC(=O)R^{13}$, —$OR^{13}$, —$S(O)_mR^{13}$, —NHC(=NH) $NHR^{13}$, —C(=NH) $NHR^{13}$, —C(=O)$NR^{13}R^{14}$, —$NR^{14}C(=O)$ $R^{13}$, =$NOR^{14}$—$NR^{14}C(=O)OR^{14}$, —$OC(=O)$ $NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, —OP(O) $(OR^{13})_2$, $C_1$–$C_4$ alkyl, $C_2$–$C_4$ alkenyl, $C_3$–$C_6$ cycloalkylmethyl, benzyl, phenethyl, phenoxy, benzyloxy, $C_7$–$C_{10}$ arylalkyl, $C_3$–$C_6$ cycloalkoxy, $C_1$–$C_4$ alkyl substituted with —$NR^{13}R^{14}$, O-protected $C_1$–$C_4$ hydroxyalkyl, methylenedioxy, ethylenedioxy, $C_1$–$C_4$ chloro or fluoroalkyl, $C_1$–$C_4$ chloro or fluoroalkoxy, $C_1$–$C_4$ alkoxycarbonyl, pyridylcarbonyloxy, $C_1$–$C_4$ alkylcarbonyl, $C_1$–$C_4$ alkylcarbonylamino, —$OCH_2CO_2H$, 2-(1-morpholino)ethoxy, or —$C(R^{14})=N(OR^{14})$;

1–3 amino acids linked together via amide bonds, said amino acid being linked via the amine or carboxylate terminus;

$C_3$–$C_{10}$ cycloalkyl substituted with 0–2 $R^{12}$ $C_1$–$C_4$ alkyl substitued with 0–2 $R^{12}$ aryl($C_1$–$C_3$ alkyl)—, substituted with 0–2 $R^{12}$;

$C_2$–$C_6$ alkoxyalkyl—, substituted with 0–2 $R^{12}$;

$C_1$–$C_4$ alkylcarbonyloxy substituted with 0–2 $R^{12}$, $C_6$–$C_{10}$ arylcarbonyloxy substituted with 0–2 $R^{12}$, a $C_5$–$C_{14}$ carbocyclic residue substituted with 0–3 $R^{12}$;

a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is selected from one or more of the following:

H, chloro, fluoro, cyano, —$CH_2N(R^{13A}) R(^{14A})$, —$N(R^{13A}) R(^{14A})$, —$OC(=O) (C_1$–$C_3$ alkyl), O-protected hydroxy, $C_2$–$C_6$ alkoxyalkyl, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, $C_7$–$C_{10}$ arylalkyl, $C_3$–$C_6$ cycloalkoxy, $C_1$–$C_4$ alkyl substituted with N-protected amine, O-protected $C_1$–$C_4$ hydroxyalkyl, methylenedioxy, ethylenedioxy, $C_1$–$C_4$ chloro or fluoroalkyl, $C_1$–$C_4$ chloro or fluoroalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, aryl($C_1$–$C_3$ alkyl), a $C_5$–$C_{14}$ carbocyclic residue; a 5- to 10-membered heterocyclic ring system containing 1 to 4 heteroatoms independently selected from oxygen, nitrogen or sulfur, said heterocyclic ring system substituted with 0–3 $R^{12A}$;

$R^{12}$, when a substituent on carbon, is selected from one or more of the following:

phenyl, benzyl, phenethyl, phenoxy, benzyloxy, chloro, fluoro, O-protected hydroxy, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene optionally substituted with —$Si(CH_3)_3$, O-protected $C_1$–$C_4$ hydroxyalkyl, methylenedioxy, ethylenedioxy, $C_1$–$C_4$ chloro or fluoroalkyl, $C_1$–$C_4$ chloro or fluoroalkyl, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2R^{13}$, 2-(1-morpholino)ethoxy, —$C(R^{14})=N(OR^{14})$; or a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6- membered ring being optionally substituted on the aliphatic carbons with fluoro, chloro, $C_1$–$C_4$ alkyl, $C_1$–$C_4$ alkoxy, O-protected hydroxy, or —$NR^{13}R^{14}$; or, when $R^{12}$ is attached to a saturated carbon atom, it may be =O or =S; or when $R^{12}$ is attached to sulfur it may be =O.

$R^{12}$, when a substituent on nitrogen, is selected from one or more of the following:

phenyl, benzyl, phenethyl, O-protected hydroxy, O-protected $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$—$NR^{13}R^{14}$, $C_2$—$C_6$ alkoxyalkyl, $C_1$–$C_4$ chloro or fluoroalkyl, $C_1$–$C_4$ alkoxycarbonyl, $C_1$–$C_4$ alkylcarbonyloxy, $C_1$–$C_4$ alkylcarbonyl, —$C(R^{14})=N(OR^{14})$;

$R^{12A}$ when a substituent on carbon, is selected from one or more of the following:

phenyl, benzyl, phenethyl, phenoxy, benzyloxy, chloro, fluoro, O-protected hydroxy, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with N-protected amino, N-protected amine, $C_2$—$C_6$ alkoxyalkyl optionally substituted with —$Si(CH_3)_3$, $C_1$–$C_4$ hydroxyalkyl, methylenedioxy, ethylenedioxy, $C_1$–$C_4$ chloro or fluoroalkyl, $C_1$–$C_4$ chloro or fluoroalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)mMe$, —$NHSO_2Me$, —$OCH_2CO_2R^{13}$, 2-(1-morpholino)ethoxy; or a 5- or 6-membered heterocyclic ring containing from 1 to 4 heteroatoms independently selected from oxygen, nitrogen or sulfur;

or $R^{12A}$ may be a 3- or 4- carbon chain attached to adjacent carbons on the ring to form a fused 5- or 6-membered ring, said 5- or 6- membered ring being optionally substituted on the aliphatic carbons with fluoro or chloro, $C_1$–$C_4$ alkyl, $C_1$–$C_4$ alkoxy, O-protected hydroxy, or N-protected amine; or, when $R^{12A}$ is attached to a saturated carbon atom, it may be =O or =S; or when $R^{12}$ is attached to sulfur it may be =O.

$R^{12A}$ when a substituent on nitrogen, is selected from one or more of the following:

phenyl, benzyl, phenethyl, O-protected hydroxy, O-protected $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, N-protected —$CH_2$-amine, N-protected amine, $C_2$–$C_6$ alkoxyalkyl, $C_1$–$C_4$ chloro or fluoroalkyl, $C_1$–$C_4$ alkoxycarbonyl, $C_1$–$C_4$ alkylcarbonyloxy, $C_1$–$C_4$ alkylcarbonyl;

$R^{13}$ is selected from:

H;

phenyl substituted with 0–3 $R^{11A}$;

benzyl substituted with 0–3 $R^{11A}$;

$C_1$–$C_6$ alkyl substituted with 0–3 $R^{11A}$;

$C_2$–$C_4$ alkenyl substituted with 0–3 $R^{11A}$;

$C_1$–$C_6$ alkylcarbonyl substituted with 0–3 $R^{11A}$;

$C_1$–$C_6$ alkoxycarbonyl substituted with 0–3 $R^{11A}$;

$C_1$–$C_6$ alkylaminocarbonyl substituted with 0–3 $R^{11A}$;

$C_3$–$C_6$ alkoxyalkyl substituted with 0–3 $R^{11A}$;

an amine protecting group when $R^{13}$ is bonded to N;

a hydroxy protecting group when $R^{13}$ is bonded to O;

$R^{14}$ is hydrogen, hydroxy, $C_1$–$C_6$ alkyl substituted with 0–3 groups selected from O-protected hydroxy, $C_1$–$C_4$ alkoxy, chloro, fluoro, N-protected amine, $C_1$–$C_6$ dialkylamine, $C_1$–$C_6$ alkoxy, $C_2$–$C_6$ alkenyl, phenyl, benzyl, an amine protecting group when $R^{14}$ is bonded to N, a hydroxy protecting group when $R^{14}$ is bonded to O;

$R^{13}$ and $R^{14}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

$R^{13A}$ and $R^{14A}$ are independently selected from: H, C$_1$–C$_6$ alkyl;

$R^{13A}$ and $R^{14A}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

$R^{15}$ is H or CH$_3$;

m is 0, 1 or 2;

said process comprising one or more of the following steps:

(1) (oxidation) contacting a compound of formula (I):

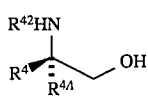  (I)

wherein:

$R^4$ and $R^{4A}$ are as defined above;

$R^{42}$ is an amine protecting group which is stable to base, oxidation, and Caulton's reagent, and which can be removed using a reagent or conditions, or combination thereof, which will not effect removal of the $R^{5A}$ and $R^{6A}$ hydroxyl protecting group from a compound of formula (V) defined below;

with 2,2,6,6-tetramethyl-1-piperidinyloxy free radical (TEMPO), sodium hypochlorite, and sodium bromide in water and a suitable aprotic solvent, preferably methylene chloride, to form a compound of the formula (II):

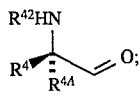  (II)

(2) (coupling) contacting a compound of formula (III):

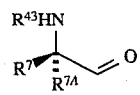  (III)

said compound of formula being prepared according to step (1), wherein:

$R^7$ and $R^{7A}$ are as defined above;

$R^{43}$ is an amine protecting group which is stable to base, oxidation, and Caulton's reagent, and which can be removed using a reagent or conditions, or combination thereof, which will not effect removal of the $R^{5A}$ and $R^{6A}$ hydroxyl protecting group from a compound of formula (V) defined below;

with a compound of formula (II) and Caulton's reagent in a suitable aprotic solvent, preferably methylene chloride, to form a compound of the formula (IV):

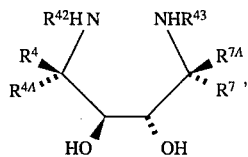  (IV)

said compound of the formula (IV) may optionally be purified by crystallization from a suitable solvent; (3) (hydroxyl protection) contacting a compound of formula (IV) with a suitable hydroxy protecting group reagent, to form a compound of formula (V):

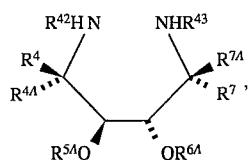  (V)

where $R^{5A}$ and $R^{6A}$ are hydroxy protecting groups, said $R^{5A}$ and $R^{6A}$ hydroxy protecting groups not being removed in the presence of a reagent or conditions, or combination thereof, effective to remove the amine protecting groups $R^{42}$ and $R^{43}$ according to step (4);

(4) (nitrogen aleprotection) contacting a compound of formula (V) with a reagent or conditions, or combination thereof, to effect the removal of the amine protecting groups $R^{42}$ and $R^{43}$, without removal of the $R^{5A}$ and $R^{6A}$ hydroxy protecting groups, to form a compound of formula (VI):

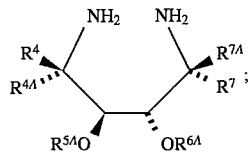  (VI)

(5) (cyclization) contacting a compound of formula (VI) with a suitable cyclizing reagent, to form a compound of formula (VII):

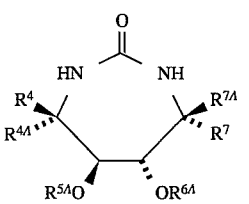  (VII)

(6) (hydroxyl deprotection) contacting a compound of formula (VII) with a reagent or conditions, or combination thereof, to effect the removal of the $R^{5A}$ and $R^{6A}$ hydroxy protecting groups, in a suitable solvent, to form a compound of formula (VIII):

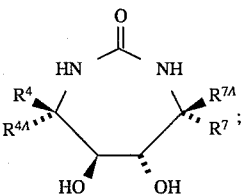  (VIII)

(7) (hydroxyl protection with cyclic ketal) contacting a compound of formula (VIII) with a suitable cyclic acetal hydroxyl protecting group reagent, in the presence of a suitable acid catalyst in a suitable solvent, to form a compound of formula (IX).

It is preferable that: the suitable hydroxy protecting group reagent in step (3) is a suitable halogen activated triethylsilyl (TES) hydroxy protecting group reagent; step (3) is carried out in the presence of a base; $R^{5A}$ and $R^{6A}$ are triethylsilyl (TES); and the reagent or conditions, or combination thereof, to effect the removal of the $R^{5A}$ and $R^{6A}$ hydroxy protecting groups in step (6) is an acid (i.e., step (6) is carried out in the presence of an acid).

The cyclic acetal hydroxyl protecting group reagent in step (7) is preferably a cyclic acetal hydroxyl protecting group reagent of formula:

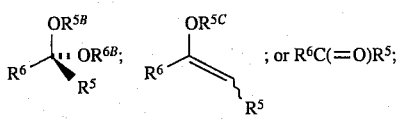

wherein:
R$^5$ and R$^6$ are defined above; and
R$^{5B}$, R$^{6B}$, and R$^{5c}$ are independently selected from C$_1$–C$_6$ alkyl or aryl; and
and step (7) is carried out in the presence of a suitable acid catalyst.

More preferably R$^{5B}$, R$^{6B}$, and R$^{5c}$ are independently selected from C$_1$–C$^3$ alkyl.

In the process of the present invention, each of the intermediates of formula (II) to (VIII), may optionally be carried through to the next step in the process without isolation prior to the next step (i.e., without isolation of the intermediate, for example, by chromatography or crystallization, between steps in the process).

As indicated above, in the process of the present invention the compounds of formula (II) and (III) may be identical such that both the compounds of formula (II) and (III) are effectively provided by the same reaction of step (1).

Preferred in the present invention is the process described above wherein:

R$^5$ and R$^6$ are independently: H, C$_1$–C$_4$ alkyl, C$_1$–C$_4$ alkoxy, C$_6$–C$_{10}$ aryl, C$_7$–C$_{14}$ arylalkyl, C$_1$–C$_4$ fluoro or chloroalkyl, C$_3$–C$_7$ cycloalkyl, or can be taken together to be keto;

alternatively, R$^5$ and R$^6$ can be taken together with the carbon to which they are attached to form a 3–7 membered saturated carbocyclic ring system;

R$^{4A}$ and R$^{7A}$ are H;

R$^4$ and R$^7$ are independently:

C$_1$–C$_8$ alkyl substituted with 0–3 R$^{11}$;
C$_2$–C$_8$ alkenyl substituted with 0–3 R$^{11}$;
C$_2$–C$_8$ alkynyl substituted with 0–3 R$^{11}$;
a C$_3$–C$_{14}$ carbocyclic ring system substituted with 0–3 R$^{11}$ or 0–3 R$^{12}$;
a 5- to 10-membered heterocyclic ring system containing 1 to 4 heteroatoms independently selected from oxygen, nitrogen or sulfur, said heterocyclic ring system being substituted with 0–2 R$^{12}$;

R$^{11}$ is selected from one or more of the following:

H, fluoro, chloro, cyano, —CH$_2$NR$^{13}$R$^{14}$ —NR$^{13}$R$^{14}$, —OR$^{13}$, C$_1$–C$_4$ alkyl, C$_2$–C$_4$ alkenyl, C$_3$–C$_6$ cycloalkylmethyl, benzyl, phenethyl, phenoxy, benzyloxy, C$_7$–C$_{10}$ arylalkyl, C$_3$–C$_6$ cycloalkoxy, C$_1$–C$_4$ alkyl substituted with —NR$^{13}$R$^{14}$ O-protected C$_1$–C$_4$ hydroxyalkyl, methylenedioxy, ethylenedioxy, C$_1$–C$_4$ fluoro or chloroalkyl, C$_1$–C$_4$ fluoro or chloroalkoxy, 2-(1-morpholino)ethoxy;
C$_3$–C$_{10}$ cycloalkyl substituted with 0–2 R$^{12}$;
C$_1$–C$_4$ alkyl substitued with 0–2 R$^{12}$;
aryl(C$_1$–C$_3$ alkyl)—, substituted with 0–2 R$^{12}$;
C$_2$–C$_6$ alkoxyalkyl—, substituted with 0–2 R$^{12}$;
a C$_5$–C$_{14}$ carbocyclic residue substituted with 0–3 R$^{12}$; or
a 5- to 10-membered heterocyclic ring system containing 1 to 4 heteroatoms independently selected from oxygen, nitrogen or sulfur, said heterocyclic ring system being substituted with 0–3 R$^{12}$;

R$^{11A}$ is:

H, fluoro, chloro, cyano, —CH$_2$N(R$^{13}$A)R($^{14A}$), —N(R$^{13A}$)R($^{14A}$), O-protected hydroxy, C$_2$–C$_6$ alkoxyalkyl, C$_1$–C$_4$ alkyl, C$_2$–C$_4$ alkenyl, C$_3$–C$_{10}$ cycloalkyl, C$_3$–C$_6$ cycloalkylmethyl, benzyl, phenethyl, phenoxy, benzyloxy, nitro, C$_7$–C$_{10}$ arylalkyl, C$_3$–C$_6$ cycloalkoxy, C$_1$–C$_4$ alkyl substituted with N-protected amine, C$_1$–C$_4$ hydroxyalkyl, methylenedioxy, ethylenedioxy, C$_1$–C$_4$ fluoro or chloroalkyl, C$_1$–C$_4$ fluoro or chloroalkoxy, 2-(1-morpholino)ethoxy, aryl(C$_1$–C$_3$ alkyl), a C$_5$–C$_{14}$ carbocyclic residue; or a 5- to 10-membered heterocyclic ring system containing 1 to 4 heteroatoms independently selected from oxygen, nitrogen or sulfur, said heterocyclic ring system substituted with 0–3 R$^{12A}$;

R$^{12}$, when a substituent on carbon, is:

phenyl, benzyl, phenethyl, phenoxy, benzyloxy, fluoro, chloro, O-protected hydroxy, cyano, C$_1$–C$_4$ alkyl, C$_3$–C$_6$ cycloalkyl, C$_3$–C$_6$ cycloalkylmethyl, C$_7$–C$_{10}$ arylalkyl, C$_1$–C$_4$ alkoxy, C$_3$–C$_6$ cycloalkoxy, —OR$^{13}$, C$_1$–C$_4$ alkyl substituted with —NR$^{13}$R$^{14}$, —NR$^{13}$R$^{14}$, C$_2$–C$_6$ alkoxyalkylene, C$_1$–C$_4$ hydroxyalkyl, methylenedioxy, ethylenedioxy, C$_1$–C$_4$ fluoro or chloroalkyl, C$_1$–C$_4$ fluoro or chloroalkoxy, 2-(1-morpholino)ethoxy, or a 5- or 6-membered heterocyclic ring containing from 1 to 4 heteroatoms independently selected from oxygen, nitrogen or sulfur;

or R$^{12}$ may be a 3- or 4- carbon chain attached to adjacent carbons on the ring to form a fused 5- or 6-membered ring, said 5- or 6- membered ring being optionally substituted on the aliphatic carbons with fluoro or chloro, C$_1$–C$_4$ alkyl, C$_1$–C$_4$ alkoxy, hydroxy, —NR$^{13}$R$^{14}$;

R$^{12}$, when a substituent on nitrogen, is:

phenyl, benzyl, phenethyl, O-protected hydroxy, C$_1$–C$_4$ hydroxyalkyl, C$_1$–C$_4$ alkoxy, C$_1$–C$_4$ alkyl, C$_3$–C$_6$ cycloalkyl, C$_3$–C$_6$ cycloalkylmethyl, —CH$_2$NR$^{13}$R$^{14}$, —NR$^{13}$R$^{14}$ C$_2$–C$_6$ alkoxyalkyl, C$_1$–C$_4$ fluoro or chloroalkyl;

R$^{12A}$, when a substituent on carbon, is:

phenyl, benzyl, phenethyl, phenoxy, benzyloxy, fluoro, chloro, O-protected hydroxy, cyano, C$_1$–C$_4$ alkyl, C$_3$–C$_6$ cycloalkyl, C$_3$–C$_6$ cycloalkylmethyl, C$_7$–C$_{10}$ arylalkyl, C$_1$–C$_4$ alkoxy, C$_3$–C$_6$ cycloalkoxy, —OR$^{13a}$, C$_1$–C$_4$ alkyl substituted with N-protected amine, N-protected amine, C$_1$–C$_5$ dialkyl amine, C$_2$–C$_6$ alkoxyalkyl, O-protected C$_1$–C$_4$ hydroxyalkyl, methylenedioxy, ethylenedioxy, C$_1$–C$_4$ fluoro or chloroalkyl, C$_1$–C$_4$ fluoro or chloroalkoxy, 2-(1-morpholino)ethoxy, a 5- or 6-membered heterocyclic ring containing from 1 to 4 heteroatoms independently selected from oxygen, nitrogen or sulfur;

or R$^{12A}$ may be a 3- or 4- carbon chain attached to adjacent carbons on the ring to form a fused 5- or 6-membered ring, said 5- or 6- membered ring being optionally substituted on the aliphatic carbons with fluoro or chloro, C$_1$–C$_4$ alkyl, C$_1$–C$_4$ alkoxy, O-protected hydroxy, or N-protected amine;

R$^{12A}$, when a substituent on nitrogen, is:

phenyl, benzyl, phenethyl, O-protected hydroxy, C$_1$–C$_4$ hydroxyalkyl, C$_1$–C$_4$ alkoxy, C$_1$–C$_4$ alkyl, C$_3$–C$_6$ cycloalkyl, C$_3$–C$_6$ cycloalkylmethyl, —CH$_2$-(N-protected amine), N-protected amine, C$_2$–C$_6$ alkoxyalkyl, or C$_1$–C$_4$ fluoro or chloro alkyl; R$^{13}$ is selected from:

H;
phenyl substituted with 0–3 R$^{11A}$;
benzyl substituted with 0–3 R$^{11A}$;
C$_1$–C$_6$ alkyl substituted with 0–3 R$^{11A}$;
C$_2$–C$_4$ alkenyl substituted with 0–3 R$^{11A}$;
C$_3$–C$_6$ alkoxyalkyl substituted with 0–3 R$^{11A}$;
an amine protecting group when R$^{13}$ is bonded to N;
a hydroxy protecting group when R$^{13}$ is bonded to O;

R$^{14}$ is selected from: hydrogen; hydroxy; C$_1$–C$_6$ alkoxy; C$_2$–C$_6$ alkenyl; phenyl; benzyl; an amine protecting group when R$^{14}$ is bonded to N; a hydroxy protecting group when R$^{14}$ is bonded to O; or C$_1$–C$_6$ alkyl substituted with 0–3 groups selected from O-protected hydroxy, C$_1$–C$_4$ alkoxy, fluoro, chloro, N-protected amine, —N(C$_1$–C$_4$ alkyl)$_2$;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected from: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

Preferred in the present invention is a process as described above wherein:

$R^4$ and $R^7$ are independently selected from the following groups:

hydrogen;

$C_1$–$C_8$ alkyl substituted with 0–3 $R^{11}$;

$C_2$–$C_8$ alkenyl substituted with 0–3 $R^{11}$;

$C_2$–$C_8$ alkynyl substituted with 0–3 $R^{11}$;

$R^{4A}$ and $R^{7A}$ are H;

$R^{11}$ is selected from one or more of the following: H, cyano, —$CH_2NR^{13}R^{14}$, —$NR^{13}R^{14}$ —$OR^{13}$, —$S(O)_mR^{13}$, $C_1$–$C_4$ alkyl, $C_2$–$C_4$ alkenyl, $C_3$–$C_{10}$ cycloalkyl substituted with 0–2 $R^{12}$, a $C_5$–$C_{14}$ carbocyclic residue substituted with 0–3 $R^{12}$ aryl($C_1$–$C_3$ alkyl)—, substituted with 0–2 $R^{12}$, aryl substituted with 0–3 $R^{12}$; or a 5- to 10-membered heterocyclic ring system containing 1 to 4 heteroatoms independently selected from oxygen, nitrogen or sulfur, said heterocyclic ring system being substituted with 0–3 $R^{12}$;

$R^{12}$, when a substituent on carbon, is selected from one or more of the following:

phenyl, benzyl, phenethyl, phenoxy, benzyloxy, P-protected hydroxy, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, sulfonamide, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene optionally substituted with —$Si(CH_3)_3$, $C_1$–$C_4$ benzyloxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, 2-(1-morpholino)ethoxy, —$C(R^{14})=N(OR^{14})$; or a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6- membered ring being optionally substituted on the aliphatic carbons with $C_1$–$C_4$ alkyl, $C_1$–$C_4$ alkoxy, O-protected hydroxy, or —$NR^{13}R^{14}$; or, when $R^{12}$ is attached to a saturated carbon atom, it may be =O or =S; or when $R^{12}$ is attached to sulfur it may be =O;

$R^{12}$, when a substituent on nitrogen, is selected from one or more of the following:

phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkylcarbonyl, —$C(R^{14})=N(OR^{14})$;

$R^{13}$ is $C_1$–$C_6$ alkyl; $C_3$–$C_6$ alkoxyalkyl; $C_2$–$C_4$ alkenyl; phenyl; or benzyl;

$R^{14}$ is benzyloxy, $C_1$–$C_6$ alkyl, $C_1$–$C_6$ alkoxy, $C_2$–$C_6$ alkenyl, phenyl, benzyl, an amine protecting group when $R^{14}$ is bonded to N, or a hydroxy protecting group when $R^{14}$ is bonded to O;

m is 0, 1 or 2.

Preferred in the present invention is a process as described above wherein:

$R^5$ and $R^6$ are methyl, ethyl, or can be taken together with the carbon to which they are attached to form cyclohexyl or cyclopentyl;

$R^4$ and $R^7$ are $C_1$–$C_8$ alkyl substituted with 0–1 $R^{11}$;

$R^{11}$ is

H; fluoro; chloro; —$OR^{13}$;

$C_3$–$C_{10}$ cycloalkyl substituted with 0–2 $R^{12}$;

aryl substituted with 0–2 $R^{12}$; or a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12}$;

$R^{12}$, when a substituent on carbon, is selected from one or more of the following:

benzyloxy, fluoro, chloro, methyl, $C_1$–$C_4$ alkoxy, $CF_3$, 2-(1-morpholino)ethoxy, cyano, $C_3$–$C_6$ cycloalkoxy, $C_1$–$C_4$ alkyl substituted with —$NR^{13}R^{14}$ —$NR^{13}R^{14}$;

$R^{12}$, when a substituent on nitrogen, is methyl;

$R^{13}$ is H, $C_1$–$C_4$ alkyl, $C_2$–$C_4$ alkenyl, or benzyl;

$R^{14}$ is H, $CF_3$, $C_1$–$C_4$ alkyl, $C_1$–$C_4$ alkoxy, $C_2$–$C_4$ alkenyl, or benzyl;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—.

Further preferred in the present invention is a process as described above wherein:

$R^5$ and $R^6$ are methyl;

$R^4$ and $R^7$ are H;

$R^4$ and $R^7$ are benzyl, fluorobenzyl, pyrrolylmethyl, methoxybenzyl, isobutyl, n-octyl, n-hexyl, dimethylaminobenzyl, thienylmethyl, pyridylmethyl, naphthylmethyl, nitrobenzyl, N-protected aminobenzyl, 4-thiazolylmethyl, O-protected hydroxybenzyl, pyridylmethyl, or naphthylmethyl.

The processes of the present invention are useful for the preparation of compounds useful as intermediates for the synthesis of cyclic HIV protease inhibitors, including cyclic urea HIV protease inhibitors. Such cyclic HIV protease inhibitors are disclosed in copending commonly assigned U.S. patent application Ser. No. 08/197,630, Lam et al., filed Feb. 16, 1994 and Lam et al., PCT International Publication Number WO 93/07,128, the disclosures of which are incorporated herein by reference. Such cyclic HIV protease inhibitors are useful for the inhibition of HIV and the treatment of HIV infection. Such cyclic HIV protease inhibitors are also useful for the inhibition of HIV in an ex vivo sample containing HIV or expected to be exposed to HIV. Thus, such cyclic HIV protease inhibitors may be used to inhibit HIV present in a body fluid sample (for example, a serum or semen sample) which contains or is suspected to contain or be exposed to HIV. Such cyclic HIV protease inhibitors are also useful as standard or reference compounds for use in tests or assays for determining the ability of an agent to inhibit viral replication and/or HIV protease, for example in a pharmaceutical research program. Thus, such cyclic HIV protease inhibitors may be used as a control or reference compound in such assays and as a quality control standard. Such cyclic HIV protease inhibitors may be provided in a commercial kit or container for use as such standard or reference compound. Since such cyclic HIV protease inhibitors exhibit specificity for HIV protease, they may also be useful as diagnostic reagents in diagnostic assays for the detection of HIV protease. Thus, inhibition of the protease activity in an assay by such a cyclic HIV protease inhibitor would be indicative of the presence of HIV protease and HIV virus.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected and may include aprotic solvents, including but not limited to polar aprotic organic solvents. Depending on the particular reaction step, suitable solvents for a particular reaction step may be selected and may include, but are not limited to, toluene, pyridine, dimethylsulfoxide (DMSO), N,N-dimethylformamide (DMF), N,N-dimethylacetamide (DMAC), diethyl ether, benzene, or tetrahydrofuran. Suitable solvents may include chlorinated organic solvents which include, but are not limited to, chloroform, methylene chloride, tetrachloroethane, butyl chloride and dichloroethane. Suitable nonchlorinated organic solvents may include, but are not limited to tetrahydrofuran (THF), diethyl ether and toluene.

Suitable protic solvents may include, by way of example and without limitation, water, methanol, and ethanol.

Suitable aprotic solvents may include, by way of example and without limitation, dimethylformamide (DMF), dimethylacetamide (DMAC), 1,3-dimethyl-3,4,5,6-tetrahydro-2(1H)-pyrimidinone (DMPU), 1,3-dimethyl-2imidazolidinone (DMI), N-methylpyrrolidinone (NMP), tetrahydrofuran (THF), methylene chloride, dimethoxyethane, ether, or hexanes.

The compounds of formula (IX) of the present invention contain a cyclic acetal hydroxyl protecting group $-OC(R^1)(R^2)O-$. As used herein, the term "cyclic acetal protecting group" includes any protecting group known in the art of organic synthesis for the protection of 1,2-diol group through formation of a cyclic acetal or cyclic ketal group. Such protecting groups include, but are not limited to, those listed in Greene and Wuts, "Protective Groups in Organic Synthesis" John Wiley & Sons, New York (1991), the disclosure of which is hereby incorporated by reference. Examples of such cyclic acetal 1,2-diol protecting groups are methylene acetal, ethylidene acetal, 2,2,2-trichloroethylidene acetal, acetonide, cycloheptylidene ketal, cyclopentylidene ketal, cyclohexylidene ketal, benzylidene acetal, phenanthrylidene, and methoxymethylene acetal. Such ketal rings or ketal protecting groups are well known in the art of organic synthesis and typically include, for example, substituted or unsubstituted carbocyclic diethers, dithioethers, mixed ethers, enol ethers or ketones.

By "cyclizing reagent" it is meant a reagent or combination of reagents and conditions that can effect the formation of a cyclic urea from the diamine of formula (VI). Examples of suitable cyclizing reagents include but are not limited to: phenyl chloroformate, phenyl tetrazoylformate, urea, phosgene, triphosgene, oxalyl chloride, N,N'-disuccinimidyl carbonate, 1,1'-carbonyldiimidazole (CDI), trichloromethyl chloroformate, and 2(S), 3-pyridinediyl thiocarbonate. A preferred cyclizing reagent is 1,1'-carbonyl diimidazole.

As used herein, a "hindered amine base" is intended to include any of a number of nitrogen containing bases wherein the nitrogen in surrounded by sterically demanding groups such that the nitrogen accessibility is reduced. Examples of hindered amine bases useful for the present invention include, by way of example and without limitation, aromatic and aliphatic amines, alkyl substituted pyridines, 1,8-diazabicyclo[2.2.2]octane (DABCO), pyridine, 4-pyrrolidinopyridine, 4-piperidinopyridine, N,N-dimethylaminopyridine (DMAP), trialkyl amines, triethylamine, N, Ndiisopropylethylamine, 1,5-diazabicyclo [4.3.0] non-5-ene (DBN), 1,8-diazabicyclo[5.4.0]undec-7-ene (DBU), or tetramethylethylenediamine (TMEDA).

As used herein, the term "amine protecting group" (or "N-protected") refers to any group known in the art of organic synthesis for the protection of amine groups. As used herein, the term "amine protecting group reagent" refers to any reagent known in the art of organic synthesis for the protection of amine groups which may be reacted with an amine to provide an amine protected with an amine protecting group. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Examples of amine protecting groups include, but are not limited to, the following:

1) acyl types such as formyl, trifluoroacetyl, phthalyl, and p-toluenesulfonyl;
2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc);
3) aliphatic carbamate types such as tertbutyloxycarbonyl (Boc), ethoxycarbonyl, diisopropylmethoxycarbonyl, and allyloxycarbonyl;
4) cyclic alkyl carbamate types such as cyclopentyloxycarbonyl and adamantyloxycarbonyl;
5) alkyl types such as triphenylmethyl and benzyl;
6) trialkylsilane such as trimethylsilane; and
7) thiol containing types such as phenylthiocarbonyl and dithiasuccinoyl.

Amine protecting groups may include, but are not limited to the following: 2,7-di-t-butyl-[9-(10,10-dioxo-10,10,10,10-tetrahydrothioxanthyl)]methyloxycarbonyl; 2-trimethylsilylethyloxycarbonyl; 2-phenylethyloxycarbonyl; 1,1-dimethyl-2,2dibromoethyloxycarbonyl; 1-methyl-1-(4-biphenylyl)ethyloxycarbonyl; benzyloxycarbonyl; pnitrobenzyloxycarbonyl; 2-(p-toluenesulfonyl)ethyloxycarbonyl; m-chloro-p-acyloxybenzyloxycarbonyl; 5benzyisoxazolylmethyloxycarbonyl; p-(dihydroxyboryl)benzyloxycarbonyl; m-nitrophenyloxycarbonyl; o-nitrobenzyloxycarbonyl; 3,5-dimethoxybenzyloxycarbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; 2-furanylmethyloxycarbonyl; phthalimide; dithiasuccinimide; 2,5-dimethylpyrrole; benzyl; 5-dibenzylsuberyl; triphenylmethyl; benzylidene; diphenylmethylene; or methanesulfonamide.

As used herein, the term "hydroxy protecting group" (or "O-protected") refers to any group known in the art of organic synthesis for the protection of hydroxyl groups. As used herein, the term "hydroxy protecting group reagent" refers to any reagent known in the art of organic synthesis for the protection of hydroxy groups which may be reacted with an hydroxy to provide an hydroxy group protected with an hydroxy protecting group. Such protecting groups include those listed in Greene and Wuts, "Protective Groups in Organic Synthesis", John Wiley & Sons, New York (1991), the disclosure of which is hereby incorporated by reference. The hydroxy protecting groups are base-stable and can include, but are not limited to acyl types, aromatic carbamate types and alkyl types. Exemplary are methyl, methoxymethyl (MOM), methylthiomethyl, benzyloxymethyl, t-butoxymethyl, 2-methoxyethoxymethyl, 2,2,2-trichloroethoxymethyl, 2-(trimethylsilyl)ethoxymethyl (SEM), tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

Suitable hydroxy protecting groups may include the following protecting groups as ethers:
tetrahydropyranyl, triphenylmethyl, benzyl, tetrahydrofuranyl, allyl, methoxymethyl (MOM), benzyloxymethyl, p-methoxybenzyloxymethyl, 2-trimethylsilylethoxymethyl (SEM), t-butoxymethyl, methylthiomethyl, 2-methoxyethoxymethyl, trichloroethoxymethyl, t-butyl, p-methoxybenzyl, t-butyldimethylsilyl, o-nitrobenzyl, p-methoxyphenyldiphenylmethyl, p-nitrobenzyl, triisopropylsilyl, t-butyldiphenylsilyl.

Conditions to remove tetrahydropyranyl, triphenylmethyl, tetrahydrofuranyl, methoxymethyl, benzyloxymethyl, p-methoxybenzyloxymethyl, 2-trimethylsilylethoxymethyl, t-butoxymethyl, methylthiomethyl, 2-methoxyethoxymethyl, trichloroethoxymethyl, t-butyl, p-methoxyphenyldiphenylmethyl, may include: (a) 1–4M HCl in anhydrous or aqueous methanol, ethanol, isopropanol, tetrahydrofuran, dioxane, or diethyl ether; (b) 1–4M $H_2SO_4$ in anhydrous or aqueous methanol, ethanol, isopropanol, tetrahydrofuran, dioxane, or diethyl ether; (c) polystyrene sulfonic acid resin in anhydrous or aqueous methanol, ethanol, isopropanol, tetrahydrofuran, dioxane, or diethyl ether; (d) 10–100% trifluoroacetic acid in dichloromethane; or (e) p-toluenesulfonic acid or camphorsulfonic acid in anhydrous or aqueous methanol, ethanol, isopropanol.

Conditions to remove benzyl, benzyloxymethyl, p-methoxybenzyloxymethyl, p-methoxybenzyl, o-nitrobenzyl, p-nitrobenzyl are: hydrogenolysis in the presence of 1–17% palladium on carbon, or palladium black. Conditions to remove o-nitrobenzyl group include irradiation of the compound at 320 nm wavelength for 5–60 minutes.

Conditions to remove 2-trimethylsilylethoxymethyl, t-butyldimethylsilyl, triisopropylsilyl, t-butyldiphenylsilyl may include: treatment of the compound with tetrabutylammonium fluoride; or hydrogen flouride pyridine complex in THF, DMF or dimethylpropyleneurea.

Conditions to remove allyl may include: isomerization of the allyl ether with $[Ir(COD)(Ph_2MeP)_2]PF_6$ or $(Ph_3P)_3RhCl$ in tetrahydrofuran, diethyl ether or dioxane followed by hydrolysis with aqueous $HgCl_2$.

All of the above mentioned deprotection reactions may be carried out at temperatures ranging from 0 degree C. to a solvent reflux.

The following abbreviations may also be used herein and are defined as follows. The abbreviation "DIBAi" means diisobutylaluminum hydride. The abbreviation "RaNi" means Raney nickel. The abbreviation "LAH" means lithium aluminum hydride. The abbreviation "1,1'-CDI" means 1,1'-carbonyldiimidazole. The abbreviation "Bn" means benzyl. The abbreviation "BOC" means t-butyl carbamate. The abbreviation "CBZ" means benzyl carbamate.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

When any variable (for example, $R^{11}$, $R^{12}$, $R^{13}$, $R^{14}$, m, etc.) occurs more than one time in any constituent or formula for a compound, its definition on each occurrence is independent of its definition at every other occurrence. Thus, for example, if a group is shown to be substituted with 0–3 $R^{11}$ then said group may optionally be substituted with up to three $R^{11}$ and $R^{11}$ at each occurrence is selected independently from the defined list of possible $R^{11}$. Also, combinations of substituents and/or variables are permissible only if such combinations result in stable compounds. Similarly, by way of example, for the group $-C(R^{11})_2-$, each of the two $R^{11}$ substituents on C is independently selected from the defined list of possible $R^{11}$.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example $-C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, cycloheptyl, adamantyl and cyclooctyl; and "biycloalkyl" is intended to include saturated bicyclic ring groups such as [3.3.0]bicyclooctane, [4.3.0]bicyclononane, [4.4.0]bicyclodecane (decalin) , [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like.

The terms "—(alkyl)—", "—(alkyenyl)—", "—(phenyl)—" and the like, refer to alkyl, alkenyl, and phenyl groups, respectively, which are connected by two bonds to the rest of the structure of Formula (II). Such groups may alternatively and equivalently be denoted as "alkylene", "alkenylene", "phenylene", and the like, respectively.

"Alkylcarbonyl" is intended to include an alkyl group of an indicated number of carbon atoms attached through a carbonyl group to the residue of the compound at the designated location. "Alkylcarbonylamino" is intended to include an alkyl group of an indicated number of carbon atoms attached through a carbonyl group to an amino bridge, where the bridge is attached to the residue of the compound at the designated location. "Alkylcarbonyloxy" is intended to include an alkyl group of an indicated number of carbon atoms attached to a carbonyl group, where the carbonyl group is attached through an oxygen atom to the residue of the compound at the designated location.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; the term "arylalkyl" represents an aryl group attached through an alkyl bridge. By way of examples: the term "$C_7$–$C_{10}$ arylalkyl" is intended to refer to an aryl group attached through a $C_1$–$C_4$ alkyl bridge to the residue of the indicated compound; the term "($C_1$–$C_3$ alkyl)aryl" is intended to refer to a $C_1$–$C_3$ alkyl group which is attached through an aryl ring to the residue of the indicated compound; the term "aryl($C_1$–$C_3$ alkyl)" is intended to refer to an aryl group attached through a $C_1$–$C_3$ alkyl group to the residue of the indicated compound.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" is intended to mean a stable 5- to 7- membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl., oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazo linyl, quinolinyl, quinoxalinyl, quinuclidinyl, carbolinyl, tetrahydrofuranyl, tetrahydro isoquinolinyl, tetrahydroquinolinyl, tetrazolyl, thianthrenyl, thiazolyl, thienyl, thiophenyl, triazinyl, xanthenyl. Also included are fused ring and spiro compounds containing, for example, the above heterocycles. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl.

When a bond to a substituent is shown to cross the bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of a given formula via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) *The Peptides*, 5:342–429, the teaching of which is hereby incorporated by reference. Modified or unusual amino acids which can be used to practice the invention include, but are not limited to, D-amino acids, hydroxylysine, 4-hydroxyproline, an N—Cbz-protected amino acid, ornithine, 2,4-diaminobutyric acid, homoarginine, norleucine, N-methylaminobutyric acid, naphthylalanine, phenylglycine, 5-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The process of the present invention is described further below.

The present invention also provides improvements in the following reactions for the synthesis of intermediates for the synthesis of cyclic urea HIV protease inhibitor compounds: TEMPO oxidation of compounds of formula (I) to compounds of formula (II) (step (1)); coupling of the compounds of formula (II) and (III) via Caulton's reagent (step (2)); formation of compounds of formula (VIII) using optimized reaction conditions and protecting group manipulation (steps (3), (4) and (6)); efficient cyclization (step (5)); protection of compounds of formula (VIII) with a ketal ring (step (7)). The present invention provides an efficient multistep process (steps (1) through (7)) for the large scale preparation of high purity compounds of formula (IX) without the need for column chromatography.

By way of example and without limitation, the present invention may be further understood by Scheme 1. This scheme details the general synthetic method for preparation of compounds of formula (IX) from compounds of formula (I).

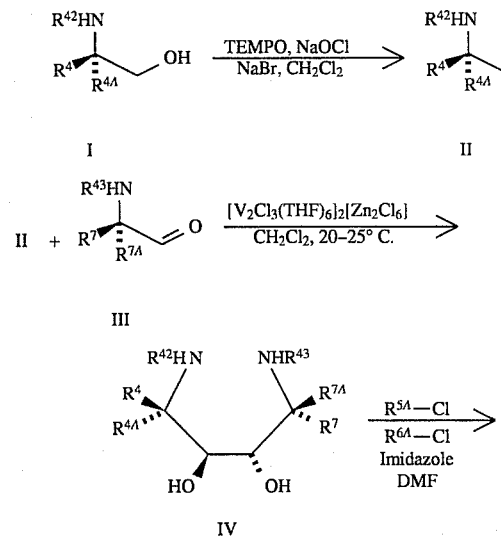

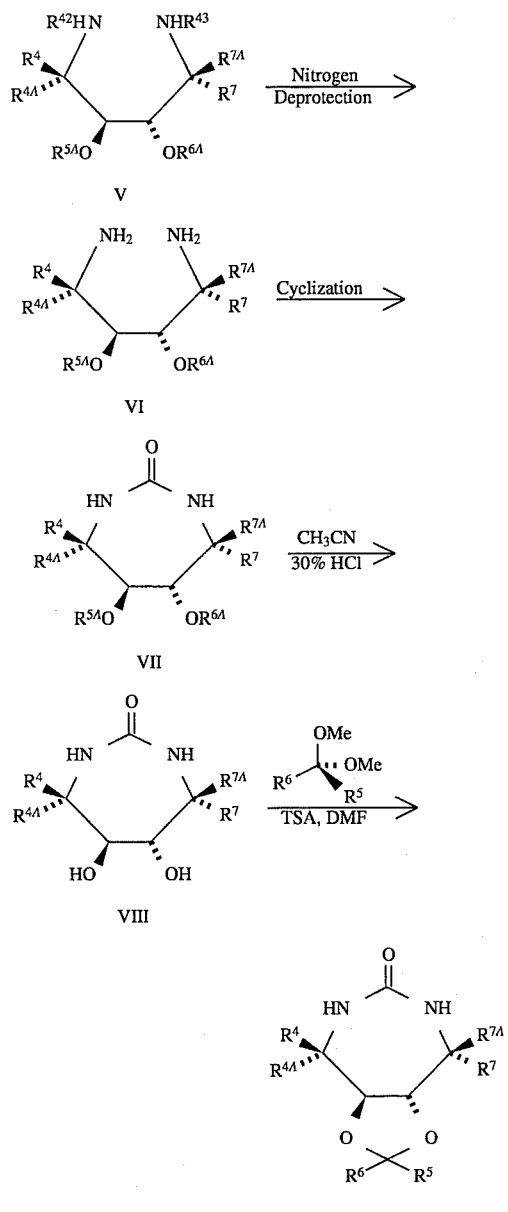

The processes of the present invention are further described below.

Step (1)(oxidation):

This step comprises the oxidation of compounds of formula (I) to compounds of formula (II). This oxidation step is conducted using TEMPO or TEMPO-like reagent (a cyclic α,α'-tetraalkyl N-oxide free radical reagent; for example, without limitation those heterocyclic N-oxides listed in the *Ardrich Structure Index*, catalog number Z23, 360–9, pages 386–387)). Preferred conditions for this step may include one or more of the following: use of a solvent (such as but not limited to: toluene, ethyl acetate, methyl acetate, methyl t-butyl ether, methylene chloride, and mixtures thereof) which effects a minimization of overoxidation and elimination of requirement for specialized high agitation equipment; use of higher NaOCl concentrations (about 0.35 to 0.55M; preferably about 0.42 to 0.49M), which effects reduction of reaction mass emulsification; use of less than 1 molar equivalent (eq) of NaBr per molar equivalent of the compound of formula (I) (molar eq ratio of about 0.1 to 0.9; preferably about 0.4 to 0.7 eq NaBr per molar equivalent of the compound of formula (I)). Use of these reaction conditions results in the formation of pure compound (II) eliminating the need for chromatographic purification.

$R^{42}$ and $R^{43}$ are independently an amine protecting groups, for example but not limited to an aromatic or aliphatic carbamate type amine protecting group. Examples of such suitable amine protecting groups include, but are not limited to: benzyloxycarbonyl (Cbz) and substituted benzyloxycarbonyls; 1-(p-biphenyl)-1-methylethoxycarbonyl; 9-fluorenylmethyloxycarbonyl (Fmoc)tert-butyloxycarbonyl (Boc); ethoxycarbonyl; diisopropylmethoxycarbonyl; allyloxycarbonyl; 2,7-di-t-butyl-[9-(10,10-dioxo-10,10,10,10-tetrahydrothioxanthyl)]methyl carbamate; 2-trimethylsilylethyl carbamate; 2-phenylethyl carbamate; 1,1-dimethyl-2,2-dibromoethyl carbamate; 1-methyl-1-(4-biphenylyl)ethyl carbamate; p-nitrobenzyl carbamate; 2-(ptoluenesulfonyl)ethyl carbamate; m-chloro-pacyloxybenzyl carbamate; 5-benzyisoxazolylmethyl carbamate; p-(dihydroxyboryl)benzyl carbamate; m-nitrophenyl carbamate; o-nitrobenzyl carbamate; 3,5-dimethoxybenzyl carbamate; 3,4-dimethoxy-6-nitrobenzyl carbamate; N'-p-toluenesulfonylaminocarbonyl; t-amyl carbamate; p-decyloxybenzyl carbamate; diisopropylmethyl carbamate; 2,2-dimethoxycarbonylvinyl carbamate; di(2-pyridyl)methyl carbamate; 2-furanylmethyl carbamate.

The product of this step may optionally be isolated in solid or solution form. For example, CBz-phenylalaninal prepared using step (1) in dichloromethane (methylene chloride) may be crystallized by solvent exchange.

A preferred solvent for step (1) is methylene chloride.

A preferred temperature range for step (1) is about −5°–10° C.

A preferred concentration of NaOCl is about 0.42–0.49M.

A preferred molar equivalent ratio of NaBr is 0.5 eq/1 eq of the compound of formula (I).

Step (2) (coupling):

This step comprises the coupling, catalyzed by Caulton's reagent ([V₂Cl₃(THF) 6]2[Zn₂Cl₆]), of two equivalents of an aldehyde of formula (II) and/or (III), to form a diol of formula (IV). See Jadhav et al., U.S. Pat. No. 5,294,720. The aldehyde product from step (1), if not isolated in solid form, may optionally be dissolved in solution in a suitable aprotic solvent, for example and without limitation, methylene chloride, 1,2-dichloroethane, chlorobenzene, THF, anisole, or toluene, or mixtures thereof. The aldehyde of formula (II) or (III) tends to be unstable and deteriorates with time.

In order to optimize the volume efficiency of this step, it is preferred that some solvent be removed from the aldehyde solution. Additionally, the solution should preferably be dried, because water will interfere with the coupling reaction. Solvent volume reduction and removal of water may be accomplished by distillation, which simultaneously removes water azeotropically. Such distillation is preferably carried out at low temperature because of the temperature sensitivity of the aldehyde. Preferred solvents for this step include ethylene chloride, 1,2-dichloroethane, toluene, or THF.

The diol of formula (IV) (the desired RSSR diastereomer) is typically obtained in purity of about 70–75% by weight on a dry basis following the reaction of step (2). The remaining mass is comprised of about 0–10% of each of the other isomers (RSSS, RRRR, RRSR).

The crude diol of formula (IV) may be isolated as a water-wet cake by precipitation using water. The water-wet cake of crude diol of formula (IV) may then be crystallized without drying from aqueous methyl ethyl ketone (MEK) (a mixture of water and MEK). Other suitable less-preferred solvents useful for the precipitation of the compound of formula (IV) are acetone, methyl isobutyl ketone, methyl isopropyl ketone, methyl propyl ketone, isopropanol, acetonitrile, methyl tertiary butyl ether. Following such crystallization, the diol of formula (IV) (the desired RSSR diastereomer) may be obtained in about 95–100% purity by weight on a dry basis, with the only impurity typically being less than 1% of the RRRR isomer. The desired RSSR diol of formula (IV) is typically obtained following crystallization as 90–95% pure.

It is preferred that the aldehyde of formula (II) and/or (III) are used in step (2) directly in solution following step (1), i. e., are not isolated.

A preferred solvent for step (2) is methylene chloride.

MEK is a preferred solvent for crystallization of the compound of formula (IV). The solvent for crystallization of the compound of formula (IV) is preferably about 100% to 50% aqueous MEK (mixture of 100 to 50 parts MEK and 0 to 50 parts water by volume), and more preferably about 87% aqueous MEK (mixture of 87 parts MEK and 13 parts water by volume). The amount of MEK is preferably about 10 to 100 parts MEK per 1 part of aldehyde charged to the reaction, by weight. The amount of MEK is more preferably about 20 parts MEK per 1 part of aldehyde charged to the reaction, by weight.

Step 3 (hydroxyl protection):

This step comprises the reaction of a compound of formula (IV) in a suitable solvent with a hydroxyl protecting group reagent. It is necessary to have the diol functionality protected during the cyclization reaction of step (5) (for example, cyclization with carbonyldiimidazole) so as to minimize byproduct formation.

It is preferred that the hydroxyl protecting group reagent be neither carcinogenic nor contain carcinogenic impurities. It is also preferred that the hydroxyl protecting group reagent yield a minimal of undesired byproducts and polymers, and can be used without requiring the purification of desired compound of formula (V).

It is preferred that the hydroxyl protecting group be stable to base and conditions which effect the removal of the amine protecting groups. The hydroxyl protecting group should allow for the fast and clean cyclization with the cyclizing reagent (for example, CDI) in step (5) to form the cyclic urea of formula ((VII).

Preferred hydroxy protecting groups are, without limitation, triethylsilyl (TES), tetrahydropyranyl, dimethyl isopropylsilyl, trimethylsilyl, or t-butyldimethylsilyl.

Preferred protecting group reagents include without limitation halogen activated trialkylsilane. A preferred protecting group reagent is triethylsilyl chloride.

Preferred solvents for step (3) (for example, using a halogen activated triethylsilane (tesilation)) include DMF, DMAC, dichloromethane, 1,2-dichloroethane, or THF, or mixtures thereof.

Preferred base catalysts include without limitation imidazole, diisopropylethylamine, and triethylamine.

It is preferred not to isolate the product of this step.

Step (4) (nitrogen deprotection):

This step comprises the removal of the amine protecting groups $R^{42}$ and $R^{43}$ by use of a reagent or conditions, or combination of reagents or conditions, which will effect the removal of the amine protecting group without removal of the $R^{5A}$ and $R^{6A}$ hydroxyl protecting groups from the compound of formula (V), to obtain the compound of formula (VI). The deprotection may be carried out in the same solvent as the cyclization reaction of step (5). The product of step (4) may be carried through to step (5) without isolation.

The preferred aleprotection reagents or conditions will include those that minimize the formation of byproducts and the addition of reagents difficult to separate from the product of formula (VI).

Preferred deprotection reagents and conditions are those typically used for catalytic hydrogenation. Palladium hydroxide on carbon, or other palladium on carbon catalysts are preferred hydrogenation catalysts.

If the product of this step is not to be isolated, the deprotection is preferably carried out in the same solvent as the cyclization reaction of step (5). The solvent for this deprotection step (4) is preferrably a polar or nonpolar aprotic solvent, for example, without limitation toluene, THF, or xylene. A preferred solvent is toluene.

If the product of this step is to be isolated, the deprotection is preferrably carried out in a solvent that dissolves the compound of formula (V).

Step (5) (cyclization):

This step comprises the cyclization of a linear diamine of formula (VI) by contacting with a suitable cyclizing reagent. The solvent for this cyclization step may be a polar or nonpolar aprotic solvent, such as, without limitation toluene, THF, or xylene.

A preferred cyclizing reagent is N,N'-carbonyldiimidazole.

Step (6) (hydroxyl deprotection):

This step comprises the deprotection of the $R^{5A}$ and $R^{6A}$ hydroxyl protecting groups of a compound of formula (VII) by contacting with an aqueous acid catalyst, to form a compound of formula (VIII). The deprotection may be conducted in a variety of suitable solvents, such as, without limitation, toluene, THF, xylene, ethylacetate, THF, isopropylalcohol or acetonitrile, or mixtures thereof.

Preferred solvents include those which allow for the concommitant formation and precipitation of compounds of formula (VIII). Preferred solvents for removal of the TES hydroxy protecting group include, but are not limited to, acetonitrile and isopropyl alcohol.

Preferred acid catalysts include without limitation a hydrogen halide, $H_2SO_4$, $H_3PO_4$, $MeSO_3H$, p-toluene sulfonic acid. A specifically preferred acid catalyst is hydrogen chloride.

Step (7) (hydroxyl protection):

This step comprises the protection of the diol hydroxyl groups of the compound of formula (VIII) with a cyclic acetal protecting group by contacting a compound of formula (VIII) with a suitable cyclic acetal protecting group reagent, such as, but not limited to, dimethoxy ketal, in the presence of an acid catalyst, to form a compound of formula (IX). Suitable acid catalysts include, without limitation, a hydrogen halide, $H_2SO_4$, $H_3PO_4$, $MeSO_3H$, p-toluene sulfonic acid. Step (7) is carried out in a suitable solvent such as, without limitation, DMF, DMAC, toluene, acetone, or cyclohexane, or mixture thereof. The urea nitrogens of the compound of formula (IX) may be subsequently alkylated.

The cyclic acetal ring may be formed with the concommitant azeotropic distillation of water and methanol as disclosed by Mash et al. *Org. Synthesis* 68 92 (1989). The final product may optionally be isolated by crystallization from a suitable solvent or combination of solvents such as, without limitation, toluene, ethylacetate, DMF, heptane, or cyclohexane, or mixture thereof.

A preferred cyclic acetal protecting group is dimethyl acetonide ($R^5$ and $R^6$=methyl) derived from dimethoxypropane.

A preferred reaction solvent is a combination of dimethylformamide (DMF) and cyclohexane.

A preferred solvent for the crystallization of the product compound of formula (IX) is a combination of DMF and ethyl acetate.

A preferred acid catalyst is p-toluene sulfonic acid.

The present invention may be further exemplified by reference to Scheme 2.

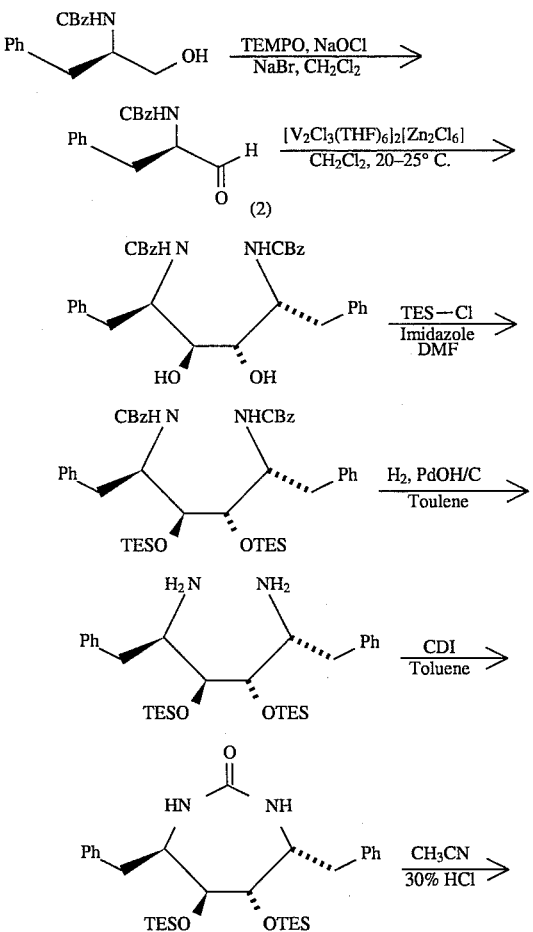

Scheme 2

-continued
Scheme 2

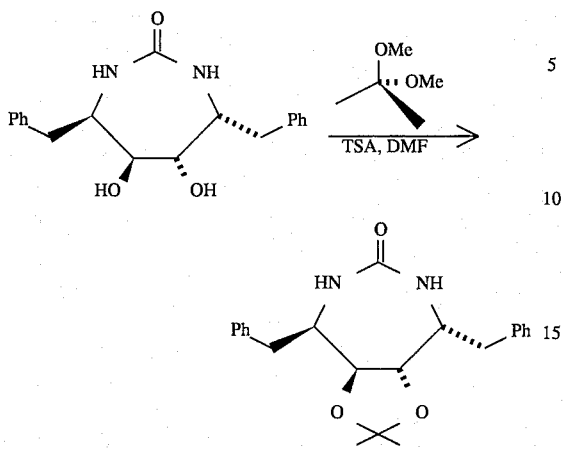

The disclosures of all of the references cited herein are hereby incorporated herein by reference in their entirety.

Using the procedures described above and outlined in Scheme 1, the claimed process can be performed in a straightforward manner to yield the compounds of formula (II) to (IX). The following examples are meant to be illustrative of the present invention. These examples are presented to exemplify the invention and are not to be construed as limiting the invention's scope.

EXAMPLE 1

Synthesis of N—Carboxybenzyl-D-phenylalaninal (General Process)

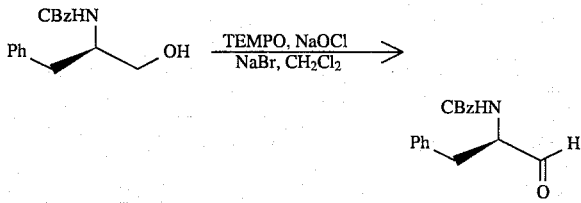

N-Carboxybenzyl-D-phenylalaninol (100 g ;0.35M) is dissolved in ethyl acetate/toluene (1:1; 1.5–2.0 L) or dichloromethane (1.0–2.0 L) and a solution of sodium bromide (18.0–25.2 g; 0.175–0.25M) in water (50–250 mL) added. The resulting two phase mixture is stirred and cooled to 0°–5° C. under a nitrogen atmosphere. 2,2,6,6-Tetramethyl-1-piperidinyloxy free radical (TEMPO) (0.055–0.55 g; 3.5–35 mM) is added. A solution of buffered sodium hypochlorite, freshly prepared by dissolving sodium bicarbonate (10–25 g; 0.12–0.3M) and commercial sodium hypochlorite solution (6–12.5% w/w; 250–584 g; 0.42–0.49M) in water (25–250 g), is added over a period of one hour with fast agitation, maintaining the reaction temperature <5° C. A solution of sodium thiosulfate pentahydrate (21.8–122 g; 0.088–0.49M) in water (64 –370 mL) is then immediately added and the reaction mixture efficiently stirred until excess oxidants have been quenched as demonstrated by starch/iodide test. Agitation is stopped and the mixture allowed to settle at 5°–10° C. After 15 minutes, the phases are separated. The organic phase is then washed with aqueous sodium bicarbonate solution (3% w/w; 500 mL) and aqueous sodium chloride solution (3% w/w; 500 mL). The organic phase is concentrated by vacuum distillation to a volume of approximately 300 mL maintaining the heating bath <20° C. Heptane (750 mL) is added and the vacuum distillation optionally continued to precipitate the product, while maintaining the heating bath <20° C. The precipitate is filtered, washed with heptane (2×200 mL) and dried under vacuum at 20° C. to constant weight to yield N-carboxybenzyl-D-phenylalaninal (90 g; 90% yield) as a white crystalline solid.

EXAMPLE 2

Synthesis of N—Carboxybenzyl-D-phenylalaninal

N-Carboxy benzyl -D-phenylalaninol (100 g; 0.35M) is dissolved in dichloromethane (1.8 L) and a solution of sodium bromide (18 g; 0.175M) in water (250 mL) is added. The resulting two phase mixture is stirred and cooled to 0°–5° C. under a nitrogen atmosphere. 2,2,6,6-Tetramethyl-1-piperidinyloxy, free radical (TEMPO) (0.055 g; 3.5 mM) is added. A solution of buffered sodium hypochlorite, freshly prepared by dissolving sodium bicarbonate (10 g; 0.12M) and commercial sodium hypochlorite solution (12.5% w/w; 250 g; 0.42M) in water (250 g), is added over a period of one hour with fast agitation, maintaining the reaction temperature <5° C. A solution of sodium thiosulfate pentahydrate (21.8 g; 0.088M) in water (64 mL) is then immediately added and the reaction mixture efficiently stirred until excess oxidants have been quenched as demonstrated by starch/iodide test. Agitation is stopped and the mixture allowed to settle at 5°–10° C. After 15 minutes, the phases are separated. The organic phase is then washed with aqueous sodium bicarbonate solution (3% w/w; 500 mL) and aqueous sodium chloride solution (3% w/w; 500 mL). The organic phase is concentrated by vacuum distillation to a volume of approximately 300 mL maintaining the heating bath <20° C. Heptane (750 mL) is added and the vacuum distillation continued again maintaining the heating bath at <20° C. A white precipitate slowly forms as the dichloromethane is removed. The distillation is continued until the dichloromethane in heptane concentration is <5% w/w. The precipitate is filtered, washed with heptane (2×200 mL) and dried under vacuum at 20° C. to constant weight to yield N-carboxybenzyl-D-phenylalaninal (90 g; 90% yield) as a white crystalline solid.

EXAMPLE 3

Synthesis of the Compound of Formula (IV) Wherein $R^{42}$ and $R^{43}$ and $R^{74}$ H, $R^4$ and $R^7$=benzyl

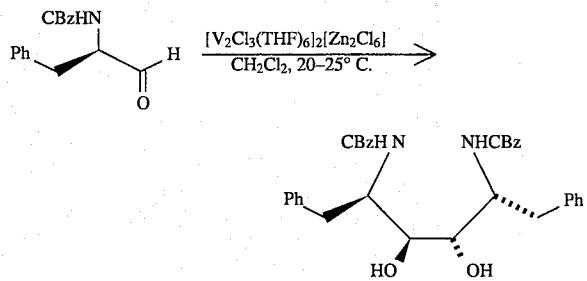

(a) Caulton's Reagent. A solution of 2 mL of 37% aqueous hydrochloric acid in 5.25 L of THF was degassed in a 22 L stirred reactor and placed under nitrogen atmosphere. Vanadium (III) chloride (437 g) was charged under nitrogen and the black slurry was refluxed for 1.5 hrs. It was allowed to cool room temperature to permit further crystallization of vanadium (III) chloride-THF complex. After standing at room temperature for 2 hours, the THF supernatant liquid was removed with exclusion of air. The complex was dissolved in 4.52 L of degassed methylene chloride and 77 g of zinc dust was added in four portions while controlling the temperature of the mildly exothermic reaction at 20°–24° C. The reaction mixture was stirred at room temperature for 1 hour, during which a green solution of Caulton's reagent formed.

(b) Coupling Reaction. A degassed solution of Cbz-D-phenylalaninal (Example 2) in methylene chloride (obtained after a TEMPO-catalyzed hypochlorite oxidation of Cbz-D-phenylalaninol with distillation to effect volume adjustment to 3.2 liters with azeotropic drying; calculated to contain 505 g of aldehyde by HPLC assay compared to a standard) was charged over a 30 min period at room temperature to the Caulton's reagent solution. The dark reaction mixture was stirred at room temperature for a further 12 hours and then discharged to a holding vessel. Dilute aqueous 1N HCl (9.23 L) was charged to the reactor and heated to 30° C. at 200–280 mm while the reaction mixture was charged over a 2 hr period. At the end of addition, the pressure was further reduced to 150 mm and held there for 45 min. The mixture was filtered and the solids were washed successively with 7.5 L of water, 7 L of 1N HCl, and five portions of 7.5 L of water. The pH of the final wash was 5. HPLC analysis showed that the desired RSSR diol isomer constituted about 73% of the diol formed. The wet cake of crude product was crystallized from a mixture of 12.4 L of methylethyl ketone (MEK) and 1.5 liters of water by heating to reflux and cooling the solution to about 20° C. and holding for about 9 hr. The temperature was further reduced to 0° C. and held for 1 hr. The product was isolated by filtration and washed with 2 L of MEK and dried at 50° C. under vacuum with nitrogen purge. The dry product amounted to 275.3 g and assayed (HPLC) at 98.3% RSSR diol. The chiral purity was 100%. The yield was 53% based on the starting aldehyde.

EXAMPLE 4

Synthesis of the Compound of Formula (IV) Wherein $R^{42}$ and $R^{43}$=CBz, $R^{4A}$ and $R^{7A}$=H, $R^4$ and $R^7$=benzyl (a) N-Carboxy benzyl-D-phenylalaninol (100 g; 0.35M) is dissolved in dichloromethane (1.8 L) and a solution of sodium bromide (18 g; 0.175M) in water (250 mL) is added. The resulting two phase mixture is stirred and cooled to 0°–5° C. under a nitrogen atmosphere. 2,2,6,6-tetramethyl-1-piperidinyloxy, free radical (TEMPO) (0.055 g; 3.5 mM) is added. A solution of buffered sodium hypochlorite, freshly prepared by dissolving sodium bicarbonate (10 g; 0.12M) and commercial sodium hypochlorite solution (12.5% w/w; 250 g; 0.42M) in water (250 g), is added over a period of one hour with fast agitation, maintaining the reaction temperature <5° C. A solution of sodium thiosulfate pentahydrate (21.8 g; 0.088M) in water (64 mL) is then immediately added and the reaction mixture efficiently stirred until excess oxidants have been quenched as demonstrated by starch/iodide test. Agitation is stopped and the mixture allowed to settle at 5°–10° C. After 15 minutes, the phases are separated. The organic phase is then washed with aqueous sodium bicarbonate solution (3% w/w; 500 mL) and aqueous sodium chloride solution (3% w/w; 500 mL). The organic phase is concentrated by vacuum distillation to a volume of approximately 600 mL maintaining the heating bath <20° C.

(b) Five batches of freshly prepared methylene chloride solution of N—Cbz-D-phenylalaninal (600–650 mL volume each; 90–95 g of aldehyde in each batch) were combined and degassed. This solution was charged over a 30 min period at room temperature to the Caulton's reagent solution, prepared as per Example 3. The dark reaction mixture was stirred at room temperature for a further 12 hours and then discharged to a holding vessel. Dilute aqueous 1N HCl (9.23 L) was charged to the reactor and heated to 30° C. at 200–280 mm while the reaction mixture was charged over a 2 hr period. At the end of addition, the pressure was further reduced to 150 mm and held there for 45 min. The mixture was filtered and the solids were washed successively with 7.5 L of water, 7 L of 1N HCl, and five portions of 7.5 L of water. The pH of the final wash was 5. HPLC analysis showed that the desired RSSR diol isomer constituted about 73% of the diol formed. The wet cake of crude product was crystallized from a mixture of 12.4 L of MEK and 1.5 liters of water by heating to reflux and cooling the solution to about 20° C. and holding for about 9 hr. The temperature was further reduced to 0° C. and held for 1 hr. The product was isolated by filtration and washed with 2 L of MEK and dried at 50° C. under vacuum with nitrogen purge. The dry product amounted to 275.3 g and assayed (HPLC) at 98.3% RSSR diol. The chiral purity was 100%. The yield was 53% based on the starting aldehyde.

EXAMPLE 5

Synthesis of the Compound of Formula (VIII) Wherein $R^{4A}$ and $R^{7A}$=H, $R^4$ and $R^7$=benzyl

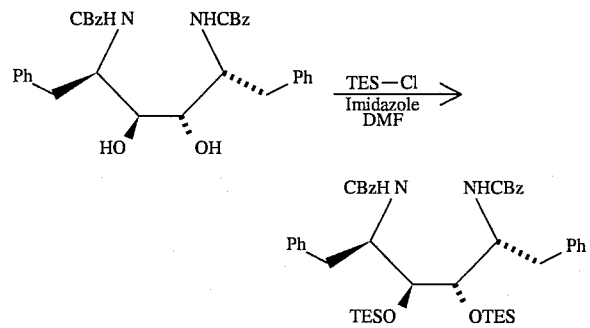

(a) TES Hydroxyl Protection. Imidazole (11 kg, 161.6 moles) was dissolved in N,N'-dimethylformamide (43.1 kg, 45.4 L). Triethylchlorosilane (20.4 kg, 135.4 moles) was added at such a rate that the temperature was maintained below 15 ° C. The compound of Example 3 (30 kg, 52.8 moles) was added in 10 charges of 3 kg each. The charges were done at such a rate that temperature was below 15 ° C. After the addition was complete the reaction mixture was heated to 35° C. Reaction was complete after 12 hours. Toluene (39.3 kg, 45 L) was added and then 47 L of USP water. Celite (3.1 kg) was added and the mixture was filtered through a 0.5 micron bag filter. Layers were separated and the top organic layer was washed with USP water (2×45 L). The resulting toluene layer was dried by distillation in vacuo of 18 L of the toluene-water azeotrope. Dry toluene (18 L) was added to bring the volume back to the original level. This solution was divided into two identical fractions, which were hydrogenated and cyclized under identical conditions described below.

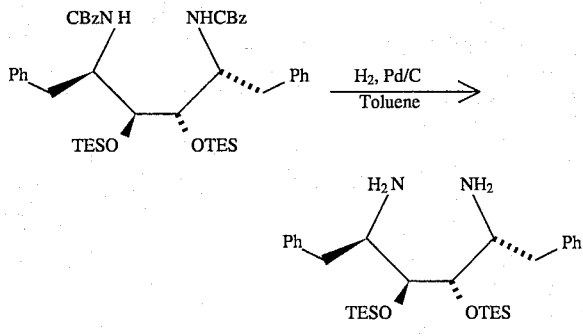

(b) Amine Deprotection. Palladium hydroxide on carbon wet (0.75 kg) was slurried into the toluene solution. Hydrogen (5 psig) was applied and the mixture was heated to 45° C. Every 15 minutes, the system was purged to help the elimination of $CO_2$ gas from the solution. Reaction was complete after 8 hours.

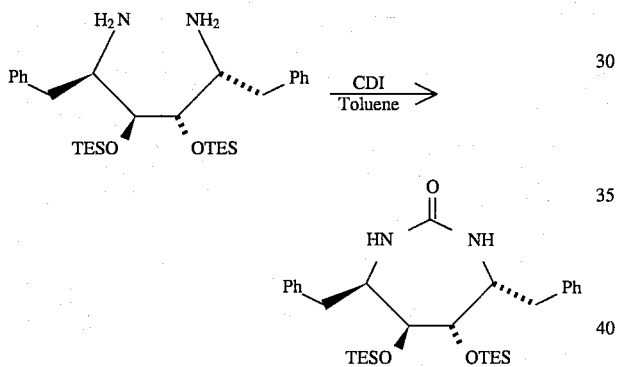

(c) Cyclization. The system was purged with nitrogen and the mixture was cooled down to 20° C. 1,1'-carbonyldiimidazole (4.5 kg) was added and the mixture stirred for 30 minutes at 20°–22° C. An aqueous 1N hydrochloric acid solution (34 kg) was then added and the mixture was filtered. Layers were separated and the top organic layer was washed with USP water (25 L).

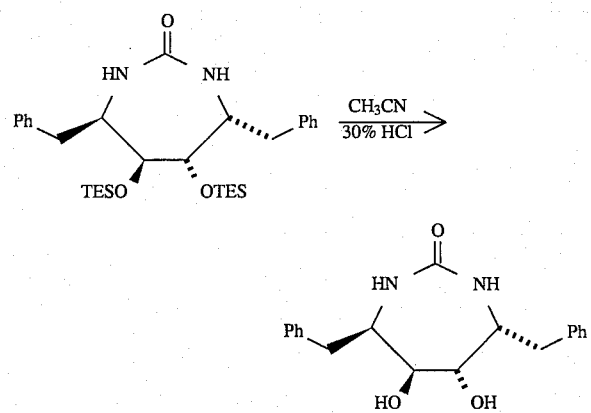

(d) Tes Hydroxyl Deprotection. The resulting organic layers of the two batches from (c) above were combined and toluene (60 L) was distilled out under vacuum and at 30°–45° C. The solvent exchange for acetonitrile was achieved by addition of acetonitrile (125 L, 98.5 kg) in five 25 L portions and distillation in vacuo of the toluene-acetonitrile azeotrope (125 L) at 28°–30° C. The reaction mixture was then cooled down to 20° C. and 1.5 L of 30% HCl was added. Reaction was complete after 16 hours. The product (title compound, Example 5) (1st crop) was filtered (first crop: 11.7 kg). The mother liquor was saved. The solid was washed with toluene (50 kg) and it was dried at 50° C. under vacuum. The two layers were separated from the mother liquor. The clear TES ether layer was discarded. The reddish acetonitrile layer was stirred at 20° C. and 24 kg of USP water was added. A second crop of the title compound was obtained which was filtered, washed with USP water (10 kg), toluene (10 kg) and dried under vacuum at 50° C. (second crop: 2.9 kg). Overall reaction yield was 78%.

Example 6

Synthesis of the Compound of Formula (IX) Wherein $R^{4A}$ and $R^{7A}$ H, $R^4$ and $R^7$=benzyl, $R^5$ and $R^6$=methyl

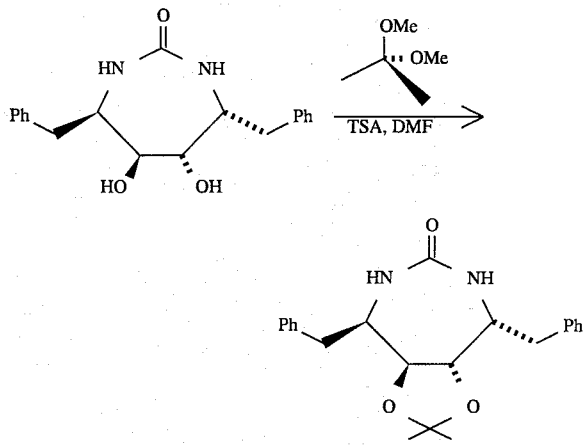

A slurry of Example 5 (14.5 kg (combined 1st and 2nd crops from step 3) 39.8 moles based on purity) and p-toluenesulfonic acid monohydrate (0.30 kg, 1.6 moles) in N,N-dimethylformamide (30.6 kg) and 2,2-dimethoxypropane (25.5 kg, 245 moles) was heated to 65° C. for 2 hours. Cyclohexane (24.1 kg) was added, and the reaction mass was distilled to 95° C. pot temperature. The reaction was cooled to 65° C., fresh 2,2-dimethoxypropane (12.7 kg, 122 moles) was added and the reaction was maintained at 65° C. for 1 hour. Cyclohexane (11.8 kg) was added, and the reaction mass was distilled to 95° C. pot temperature. The reaction was cooled to 65° C., fresh 2,2-dimethoxypropane ( 12.7 kg, 122 moles) was added and the reaction was maintained at 65° C. for 1 hour. Cyclohexane (11.8 kg) was added, and the reaction mass was distilled to 95° C. pot temperature. The reaction mass was cooled to 60° C. and was verified to be complete. Sodium hydroxide (10N, 0.095 kg, 2.4 moles) was added, and the reaction mass was concentrated by distillation at 75 mm Hg to remove residual cyclohexane and 2,2-dimethoxypropane. Water (60 L) and ethyl acetate (88.0 kg) were added and the reaction mass was heated to 65° C. and the aqueous phase was removed. Water was added and the reaction mass was heated to 65° C. and the aqueous phase was removed. The organic phase was distilled to approximately half of the original volume at 70°–80° C. Fresh ethyl acetate was added and the distillation was continued to a final volume of approximately 45 L. The reaction mass was cooled over 2 hours to 25° C., held for 0.5 hour, cooled over 1 hour to 0–5° C. and held for 0.5 hour. The resulting slurry was isolated by vacuum filtration and washed with a cold (0°–10° C.) mixture of heptane (62.6 kg) and ethyl acetate (27.7 kg). The product was dried in a 50° C. vacuum oven to constant mass, to provide 11.2 kg (76.0% of theoretical) of the title compound as a white crystalline solid.

EXAMPLE 7

Synthesis of the Compound of Formula (IX) Wherein $R^{4A}$ and $R^{7A}$=H, $R^4$ and $R^7$=benzyl, $R^5$ and $R^6$=methyl, From Di-TES-protected Cyclic Urea Crude di-TES-protected cyclic urea in solution in toluene, obtained from step (c) of Example 5 (the compound of formula (VII) wherein $R^{4A}$ and $R^{7A}$ H, =$R^4$ and $R^7$=benzyl, was evaporated in vacuo. The crude dried di-TES-protected cyclic urea (52.8 g, 0.0971 moles) was dissolved in 200 mL of N,N'-dimthylformamide under nitrogen atmosphere. Then camphorsulfonic acid (4.5 grams, 0.0194 moles) and dimethoxy propane (101 g, 0.971 moles) were added. The mixture was stirred at 45° C. for 48 h. The reaction was worked up with 300 mL of EtOAc and 300 mL of water. The aqueous layer was extracted with 100 mL of EtOAc. The combined organic layer was washed with saturated solution of NaHCO$_3$ (2×150 mL), dried with Na$_2$SO$_4$ and the solvent was partially removed. The title compound precipitated as a white solid (8.71 g, 25%).

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention. The present invention may be embodied in other specific forms without departing from the spirit or essential attributes thereof and, accordingly, reference should be made to the appended claims as further indicating the scope of the invention.

What is claimed is:

1. A process for the preparation of compounds of formula (IX):

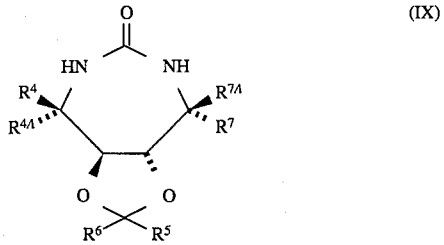

wherein:
$R^4$ and $R^7$ are independently selected from the following groups: hydrogen;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;

a $C_3$–$C_{14}$ carbocyclic ring system substituted with 0–3 $R^{11}$ or 0–3 $R^{12}$;

$R^{4A}$ and $R^{7A}$ are independently selected from the following groups:
hydrogen;
$C_1$–$C_4$ alkyl substituted with 0–6 chloro or fluoro or 0–3 $C_1$–$C_2$ alkoxy;
benzyl substituted with 0–6 chloro or fluoro or 0–3 $C_1$–$C_2$ alkoxy;
—OR$^{13}$; —SR$^{13}$; CO$_2$R$^{13}$;

$R^4$ and $R^{4A}$ can alternatively join to form a 5–7 membered carbocyclic ring substituted with 0–2 $R^{12}$;

$R^7$ and $R^{7A}$ can alternatively join to form a 5–7 membered carbocyclic ring substituted with 0–2 $R^{12}$;

$R^5$ and $R^6$ are independently H, $C_1$–$C_4$ alkyl, $C_1$–$C_4$ alkoxy, $C_6$–$C_{10}$ aryl, $C_7$–$C_{14}$ arylalkyl, $C_3$–$C_7$ cycloalkyl, or, alternately, $R^1$ and $R^2$ can be taken together with the carbon to which they are attached to form a 3–7 membered saturated carbocyclic ring system or can be taken together to be keto;

$R^{11}$ is selected from one or more of the following:
H, chloro, fluoro, cyano, —CH$_2$NR$^{13}$R$^{14}$, —NR$^{13}$R$^{14}$, —CO$_2$R$^{13}$, —OC(=O)R$^{13}$, —OR$^{13}$, —S(O)$_m$R$^{13}$, —NHC(=NH)NHR$^{13}$, —C(=NH)NHR$^{13}$, —C(=O)NR$^{13}$R$^{14}$, —NR$^{14}$C(=O)R$^{13}$, =NOR$^{14}$, —NR$^{14}$C(=O)OR$^{14}$, —OC(=O)NR$^{13}$R$^{14}$, —NR$^{13}$C(=O)NR$^{13}$R$^{14}$, —NR$^{14}$SO$_2$NR$^{13}$R$^{14}$, —NR$^{14}$SO$_2$R$^{13}$, —SO$_2$NR$^{13}$R$^{14}$, —OP(O) (OR$^{13}$)$_2$, $C_1$–$C_4$ alkyl, $C_2$–$C_4$ alkenyl, $C_3$–$C_6$ cycloalkylmethyl, benzyl, phenethyl, phenoxy, benzyloxy, $C_7$–$C_{10}$ arylalkyl, $C_3$–$C_6$ cycloalkoxy, $C_1$–$C_4$ alkyl substituted with —NR$^{13}$R$^{14}$, O-protected $C_1$–$C_4$ hydroxyalkyl, methylenedioxy, ethylenedioxy, $C_1$–$C_4$ chloro or fluoroalkyl, $C_1$–$C_4$ chloro or fluoroalkoxy, $C_1$–$C_4$ alkoxycarbonyl, pyridylcarbonyloxy, $C_1$–$C_4$ alkylcarbonyl, $C_1$–$C_4$ alkylcarbonylamino, —OCH$_2$CO$_2$H, 2-(1-morpholino)ethoxy, or —C(R$^{14}$)=N(OR$^{14}$);

1–3 amino acids linked together via amide bonds, said amino acid being linked via the amine or carboxylate terminus;
$C_3$–$C_{10}$ cycloalkyl substituted with 0–2 $R^{12}$;
$C_1$–$C_4$ alkyl substituted with 0–2 $R^{12}$;
aryl($C_1$–$C_3$ alkyl)—, substituted with 0–2 $R^{12}$;
$C_2$–$C_6$ alkoxyalkyl—, substituted with 0–2 $R^{12}$;
$C_1$–$C_4$ alkylcarbonyloxy substituted with 0–2 $R^{12}$,
$C_6$–$C_{10}$ arylcarbonyloxy substituted with 0–2 $R^{12}$;
a $C_5$–$C_{14}$ carbocyclic residue substituted with 0–3 $R^{12}$;

$R^{11A}$ is selected from one or more of the following:
H, chloro, fluoro, cyano, —CH$_2$N(R$^{13A}$)R$^{(14A)}$, —N(R$^{13A}$)R$^{(14A)}$, —OC(=O) ($C_1$–$C_3$ alkyl), O-protected hydroxy, $C_2$–$C_6$ alkoxyalkyl, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, $C_7$–$C_{10}$ arylalkyl, $C_3$–$C_6$ cycloalkoxy, $C_1$–$C_4$ alkyl substituted with N-protected amine, O-protected $C_1$–$C_4$ hydroxyalkyl, methylenedioxy, ethylenedioxy, $C_1$–$C_4$ chloro or fluoroalkyl, $C_1$–$C_4$ chloro or fluoroalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, aryl($C_1$–$C_3$ alkyl), a $C_5$–$C_{14}$ carbocyclic residue;

$R^{12}$, when a substituent on carbon, is selected from one or more of the following:

phenyl, benzyl, phenethyl, phenoxy, benzyloxy, chloro, fluoro, O-protected hydroxy, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene optionally substituted with —$Si(CH_3)_3$, O-protected $C_1$–$C_4$ hydroxyalkyl, methylenedioxy, ethylenedioxy, $C_1$–$C_4$ chloro or fluoroalkyl, $C_1$–$C_4$ chloro or fluoroalkyl, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2R^{13}$, 2-(1-morpholino)ethoxy, —$C(R^{14})=N(OR^{14})$; or or $R^{12}$ may be a 3- or 4- carbon chain attached to adjacent carbons on the ring to form a fused 5- or 6-membered ring, said 5- or 6- membered ring being optionally substituted on the aliphatic carbons with fluoro, chloro, $C_1$–$C_4$ alkyl, $C_1$–$C_4$ alkoxy, O-protected hydroxy, or —$NR^{13}R^{14}$; or, when $R^{12}$ is attached to a saturated carbon atom, it may be =O or =S;

or when $R^{12}$ is attached to sulfur it may be =O.

$R^{12}$, when a substituent on nitrogen, is selected from one or more of the following:

phenyl, benzyl, phenethyl, O-protected hydroxy, O-protected $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ chloro or fluoroalkyl, $C_1$–$C_4$ alkoxycarbonyl, $C_1$–$C_4$ alkylcarbonyloxy, $C_1$–$C_4$ alkylcarbonyl, —$C(R^{14})=N(OR^{14})$;

$R^{12A}$, when a substituent on carbon, is selected from one or more of the following:

phenyl, benzyl, phenethyl, phenoxy, benzyloxy, chloro, fluoro, O-protected hydroxy, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with N-protected amino, N-protected amine, $C_2$–$C_6$ alkoxyalkyl optionally substituted with —$Si(CH_3)_3$, $C_1$–$C_4$ hydroxyalkyl, methylenedioxy, ethylenedioxy, $C_1$–$C_4$ chloro or fluoroalkyl, $C_1$–$C_4$ chloro or fluoroalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mMe$, —$NHSO_2Me$, —$OCH_2CO_2R^{13}$, 2-(1-morpholino)ethoxy;

or $R^{12A}$ may be a 3- or 4- carbon chain attached to adjacent carbons on the ring to form a fused 5- or 6-membered ring, said 5- or 6- membered ring being optionally substituted on the aliphatic carbons with fluoro or chloro, $C_1$–$C_4$ alkyl, $C_1$–$C_4$ alkoxy, O-protected hydroxy, or N-protected amine; or, when $R^{12A}$ is attached to a saturated carbon atom, it may be =O or =S; or when $R^{12}$ is attached to sulfur it may be =O.

$R^{12A}$, when a substituent on nitrogen, is selected from one or more of the following:

phenyl, benzyl, phenethyl, O-protected hydroxy, O-protected $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, N-protected —$CH_2$-amine, N-protected amine, $C_2$–$C_6$ alkoxyalkyl, $C_1$–$C_4$ chloro or fluoroalkyl, $C_1$–$C_4$ alkoxycarbonyl, $C_1$–$C_4$ alkylcarbonyloxy, $C_1$–$C_4$ alkylcarbonyl;

$R^{13}$ is selected from: H;
phenyl substituted with 0–3 $R^{11A}$;
benzyl substituted with 0–3 $R^{11A}$;
$C_1$–$C_6$ alkyl substituted with 0–3 $R^{11A}$;
$C_2$–$C_4$ alkenyl substituted with 0–3 $R^{11A}$;
$C_1$–$C_6$ alkylcarbonyl substituted with 0–3 $R^{11A}$;
$C_1$–$C_6$ alkoxycarbonyl substituted with 0–3 $R^{11A}$;
$C_1$–$C_6$ alkylaminocarbonyl substituted with 0–3 $R^{11A}$;
$C_3$–$C_6$ alkoxyalkyl substituted with 0–3 $R^{11A}$;
an amine protecting group when $R^{13}$ is bonded to N;
a hydroxy protecting group when $R^{13}$ is bonded to O;

$R^{14}$ is hydrogen, hydroxy, $C_1$–$C_6$ alkyl substituted with 0–3 groups selected from O-protected hydroxy, $C_1$–$C_4$ alkoxy, chloro, fluoro, N-protected amine, $C_1$–$C_6$ dialkylamine, $C_1$–$C_6$ alkoxy, $C_2$–$C_6$ alkenyl, phenyl, benzyl, an amine protecting group when $R^{14}$ is bonded to N, a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected from: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

said process comprising the following steps:

(1) contacting a compound of formula (I):

wherein:

$R^{42}$ is an amine protecting group which is stable to base, oxidation, and $(V_2Cl_3(THF)_6)_2(Zn_2Cl_6)$, and which can be removed using a reagent or conditions, or combination thereof, which will not effect removal of the $R^{5A}$ and $R^{6A}$ hydroxyl protecting group from a compound of formula (V) defined below;

with α,α'-tetraalkyl N-oxide free radical, sodium hypochlorite, and sodium bromide, in a suitable aprotic solvent, to form a compound of the formula (II):

(2) contacting a compound of formula (III):

wherein:

$R^{43}$ is an amine protecting group which is stable to base, oxidation, and $(V_2Cl_3(THF)_6)_2(Zn_2Cl_6)$, and which can be removed using a reagent or conditions, or combination thereof, which will not effect removal of the $R^{5A}$ and $R^{6A}$ hydroxyl protecting group from a compound of formula (V) defined below;

with a compound of formula (II) and $(V_2Cl_3(THF)_6)_2(Zn_2Cl_6)$ in a suitable aprotic solvent, to form a compound of the formula (IV):

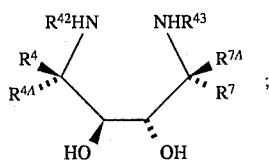

(3) contacting a compound of formula (IV) with a suitable hydroxy protecting group reagent, to form a compound of formula (V):

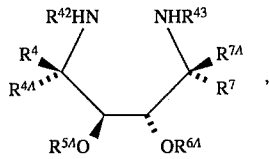

wherein:

$R^{5A}$ and $R^{6A}$ are hydroxy protecting groups, said $R^{5A}$ and $R^{6A}$ hydroxy protecting groups not being removed in the presence of a reagent or conditions, or combination thereof, effective to remove the amine protecting groups $R^{42}$ and $R^{43}$ according to step (4);

(4) contacting a compound of formula (V) with a reagent or conditions, or combination thereof, to effect the removal of the amine protecting groups $R^{42}$ and $R^{43}$, without removal of the $R^{5A}$ and $R^{6A}$ hydroxy protecting groups, to form a compound of formula (VI):

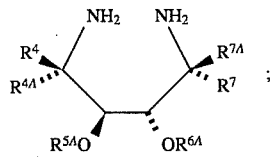

(5) contacting a compound of formula (VI) with a suitable cyclizing reagent, to form a compound of formula (VII):

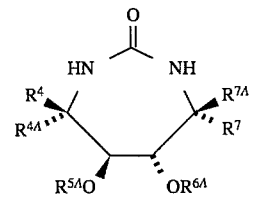

(6) contacting a compound of formula (VII) with a reagent or conditions, or combination thereof, to effect the removal of the $R^{5A}$ and $R^{6A}$ hydroxy protecting groups, in a suitable solvent, to form a compound of formula (VIII):

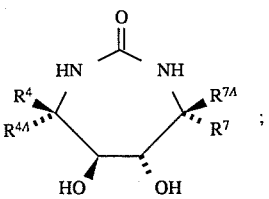

(7) contacting a compound of formula (VIII) with a suitable cyclic acetal hydroxyl protecting group reagent, in the presence of a suitable acid catalyst in a suitable solvent, to form a compound of formula (IX).

2. A process of claim 1 wherein:

$R^5$ and $R^6$ are independently: H, $C_1$–$C_4$ alkyl, $C_1$–$C_4$ alkoxy, $C_6$–$C_{10}$ aryl, $C_7$–$C_{14}$ arylalkyl, $C_1$–$C_4$ fluoro or chloroalkyl, $C_3$–$C_7$ cycloalkyl, or can be taken together to be keto;

alternatively, $R^5$ and $R^6$ can be taken together with the carbon to which they are attached to form a 3–7 membered saturated carbocyclic ring system;

$R^{4A}$ and $R^{7A}$ are H;

$R^4$ and $R^7$ are independently:
  $C_1$–$C_8$ alkyl substituted with 0–3 $R^{11}$;
  $C_2$–$C_8$ alkenyl substituted with 0–3 $R^{11}$;
  $C_2$–$C_8$ alkynyl substituted with 0–3 $R^{11}$;
  a $C_3$–$C_{14}$ carbocyclic ring system substituted with 0–3 $R^{11}$ or 0–3 $R^{12}$;

$R^{11}$ is selected from one or more of the following:
  H, fluoro, chloro, cyano, —$CH_2NR^{13}R^{14}$, —$NR^{13}R^{14}$, —$OR^{13}$, $C_1$–$C_4$ alkyl, $C_2$–$C_4$ alkenyl, $C_3$–$C_6$ cycloalkylmethyl, benzyl, phenethyl, phenoxy, benzyloxy, $C_7$–$C_{10}$ arylalkyl, $C_3$–$C_6$ cycloalkoxy, $C_1$–$C_4$ alkyl substituted with —$NR^{13}R^{14}$, O-protected $C_1$–$C_4$ hydroxyalkyl, methylenedioxy, ethylenedioxy, $C_1$–$C_4$ fluoro or chloroalkyl, $C_1$–$C_4$ fluoro or chloroalkoxy, 2-(1-morpholino)ethoxy;
  $C_3$–$C_{10}$ cycloalkyl substituted with 0–2 $R^{12}$;
  $C_1$–$C_4$ alkyl substituted with 0–2 $R^{12}$;
  aryl($C_1$–$C_3$ alkyl)—, substituted with 0–2 $R^{12}$;
  $C_2$–$C_6$ alkoxyalkyl—, substituted with 0–2 $R^{12}$;
  a $C_5$–$C_{14}$ carbocyclic residue substituted with 0–3 $R^{12}$;

$R^{11A}$ is:
  H, fluoro, chloro, cyano, —$CH_2N(R^{13A})R(^{14A})$, —$N(R^{13A})R(^{14A})$, O-protected hydroxy, $C_2$–$C_6$ alkoxyalkyl, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl substituted with N-protected amine, $C_1$–$C_4$ hydroxyalkyl, methylenedioxy, ethylenedioxy, $C_1$–$C_4$ fluoro or chloroalkyl, $C_1$–$C_4$ fluoro or chloroalkoxy, 2-(1-morpholino)ethoxy, aryl($C_1$–$C_3$ alkyl), a $C_5$–$C_{14}$ carbocyclic residue;

$R^{12}$ when a substituent on carbon, is:
  phenyl, benzyl, phenethyl, phenoxy, benzyloxy, fluoro, chloro, O-protected hydroxy, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene, $C_1$–$C_4$ hydroxyalkyl, methylenedioxy, ethylenedioxy, $C_1$–$C_4$ fluoro or chloroalkyl, $C_1$–$C_4$ fluoro or chloroalkoxy, 2-(1-morpholino)ethoxy,
  or $R^{12}$ may be a 3- or 4- carbon chain attached to adjacent carbons on the ring to form a fused 5- or 6-membered ring, said 5- or 6- membered ring being optionally substituted on the aliphatic carbons with fluoro or chloro, $C_1$–$C_4$ alkyl, $C_1$–$C_4$ alkoxy, hydroxy, —$NR^{13}R^{14}$;

$R^{12}$ when a substituent on nitrogen, is: phenyl, benzyl, phenethyl, O-protected hydroxy, $C_1$–$C_4$, hydroxyalkyl, $C_1$–$C_4$ alkoxy, $C_1$–$C_4$ alkyl, $C_3$–$C_6$ cycloalkyl $C_3$–$C_6$ cycloalkylmethyl, —$CH_2NR^{13}R^{14}$ —$NR^{13}R^{14}$, $C_2$–$C_6$ alkoxyalkyl, $C_1$–$C_4$ fluoro or chloroalkyl;

$R^{12A}$ when a substituent on carbon, is:
  phenyl, benzyl, phenethyl, phenoxy, benzyloxy, fluoro, chloro, O-protected hydroxy, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13a}$, $C_1$–$C_4$ alkyl substituted with N-protected amine, N-protected amine, $C_1$–$C_5$ dialkyl amine, $C_2$–$C_6$ alkoxyalkyl, O-protected $C_1$–$C_4$ hydroxyalkyl, methylenedioxy, ethylenedioxy, $C_1$–$C_4$ fluoro or chloroalkyl, $C_1$–$C_4$ fluoro or chloroalkoxy, 2-(1-morpholino)ethoxy, or $R^{12A}$ may be a 3- or 4- carbon chain attached to adjacent carbons on the ring to form a fused 5- or 6-membered ring, said 5- or 6- membered ring being optionally substituted on the aliphatic carbons with fluoro or chloro, $C_1$–$C_4$ alkyl, $C_1$–$C_4$ alkoxy, O-protected hydroxy, or N-protected amine;

$R^{12A}$ when a substituent on nitrogen, is:
  phenyl, benzyl, phenethyl, O-protected hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2$—(N-protected amine), N-protected amine, $C_2$–$C_6$ alkoxyalkyl, or $C_1$–$C_4$ fluoro or chloro alkyl;

$R^{13}$ is selected from:
  H;
  phenyl substituted with 0–3 $R^{11A}$;
  benzyl substituted with 0–3 $R^{11A}$;
  $C_1$–$C_6$ alkyl substituted with 0–3 $R^{11A}$;
  $C_2$–$C_4$ alkenyl substituted with 0–3 $R^{11A}$;
  $C_3$–$C_6$ alkoxyalkyl substituted with 0–3 $R^{11A}$;
  an amine protecting group when $R^{13}$ is bonded to N;
  a hydroxy protecting group when $R^{13}$ is bonded to O;

$R^{14}$ is selected from: hydrogen; hydroxy; $C_1$–$C_6$ alkoxy; $C_2$–$C_6$ alkenyl; phenyl; benzyl; an amine protecting group when $R^{14}$ is bonded to N; a hydroxy protecting group when $R^{14}$ is bonded to O; or $C_1$–$C_6$ alkyl substituted with 0–3 groups selected from O-protected hydroxy, $C_1$–$C_4$ alkoxy, fluoro, chloro, N-protected amine, —N ($C_1$–$C_4$ alkyl)$_2$;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected from: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

3. A process of claim 1 wherein:

$R^4$ and $R^7$ are independently selected from the following groups:
  hydrogen;
  $C_1$–$C_8$ alkyl substituted with 0–3 $R^{11}$;
  $C_2$–$C_8$ alkenyl substituted with 0–3 $R^{11}$;
  $C_2$–$C_8$ alkynyl substituted with 0–3 $R^{11}$;

$R^{4A}$ and $R^{7A}$ are H;

$R^{11}$ is selected from one or more of the following:
  H, cyano, —$CH_2NR^{13}R^{14}$, —$NR^{13}R^{14}$, -$OR^{13}$, —S$(O)_mR^{13}$, $C_1$–$C_4$ alkyl, $C_2$–$C_4$ alkenyl, $C_3$–$C_{10}$ cycloalkyl substituted with 0–2 $R^{12}$, a $C_5$–$C_{14}$ carbocyclic residue substituted with 0–3 $R^{12}$, aryl($C_1$–$C_3$ alkyl)—, substituted with 0–2 $R^{12}$ aryl substituted with 0–3 $R^{12}$;

$R^{12}$, when a substituent on carbon, is selected from one or more of the following:
  phenyl, benzyl, phenethyl, phenoxy, benzyloxy, O-protected hydroxy, cyano, $C_1$–$C_4$ alkyl, $C_3$–$C_6$ cycloalkyl, $C_3$–$C_6$ cycloalkylmethyl, $C_7$–$C_{10}$ aralkyl, $C_1$–$C_4$ alkoxy, sulfonamide, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene optionally substituted with —$Si(CH_3)_3$, $C_1$–$C_4$ benzyloxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, 2-(1-morpholino)ethoxy, —$C(R^{14})$=N $(OR^{14})$; or or $R^{12}$ may be a 3- or 4- carbon chain attached to adjacent carbons on the ring to form a fused 5- or 6-membered ring, said 5- or 6- membered ring being optionally substituted on the aliphatic carbons with $C_1$–$C_4$ alkyl, $C_1$–$C_4$ alkoxy, O-protected hydroxy, or —$NR^{13}R^{14}$; or, when $R^{12}$ is attached to a saturated carbon atom, it may be =O or =S; or when $R^{12}$ is attached to sulfur it may be =O;

$R^{12}$, when a substituent on nitrogen, is selected from one or more of the following:
  phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkylcarbonyl, —$C(R^{14})$=N $(OR^{14})$;

$R^{13}$ is $C_1$–$C_6$ alkyl; $C_3$–$C_6$ alkoxyalkyl; $C_2$–$C_4$ alkenyl; phenyl; or benzyl;

$R^{14}$ is benzyloxy, $C_1$–$C_6$ alkyl, $C_1$–$C_6$ alkoxy, $C_2$–$C_6$ alkenyl, phenyl, benzyl, an amine protecting group when $R^{14}$ is bonded to N, or a hydroxy protecting group when $R^{14}$ is bonded to O;

m is 0, 1 or 2.

4. A process of claim 1 wherein:

$R^5$ and $R^6$ are methyl, ethyl, or can be taken together with the carbon to which they are attached to form cyclohexyl or cyclopentyl;

$R^{4A}$ and $R^{7A}$ are H;

$R^4$ and $R^7$ are $C_1$–$C_8$ alkyl substituted with 0–1 $R^{11}$;

$R^{11}$ is
  H; fluoro; chloro;-$OR^{13}$;
  $C_3$–$C_{10}$ cycloalkyl substituted with 0–2 $R^{12}$
  aryl substituted with 0–2 $R^{12}$ $R^{12}$, when a substituent on carbon, is selected from one or more of the following:
  benzyloxy, fluoro, chloro, methyl, $C_1$–$C_4$ alkoxy, $CF_3$, 2-(1-morpholino)ethoxy, cyano, $C_3$–$C_6$ cycloalkoxy, $C_1$–$C_4$ alkyl substituted with —$NR^{13}R^{14}$, —$NR^{13}R^{14}$;

$R^{12}$ when a substituent on nitrogen, is methyl;

$R^{13}$ is H, $C_1$–$C_4$ alkyl, $C_2$–$C_4$ alkenyl, or benzyl;

$R^{14}$ is H, $CF_3$, $C_1$–$C_4$ alkyl, $C_1$–$C_4$ alkoxy, $C_2$–$C_4$ alkenyl, or benzyl;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—.

5. A process of claim 1 wherein:

$R^5$ and $R^6$ are methyl;

$R^{4A}$ and $R^{7A}$ are H;

$R^4$ and $R^7$ are benzyl, fluorobenzyl, pyrrolylmethyl, methoxybenzyl, isobutyl, n-octyl, n-hexyl, dimethylaminobenzyl, thienylmethyl, pyridylmethyl, naphthylmethyl, nitrobenzyl, N-protected aminobenzyl, 4-thiazolylmethyl, O-protected hydroxybenzyl, pyridylmethyl, or naphthylmethyl.

6. A process of claim 1 wherein:

the cyclic acetal hydroxyl protecting group reagent in step (7) is a compound of formula:

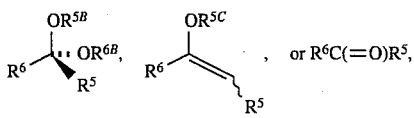

wherein:

R$^5$ and R$^6$ are independently H, C$_1$–C$_4$ alkyl, C$_1$–C$_4$ alkoxy, C$_6$–C$_{10}$ aryl, C$_7$–C$_{14}$ arylalkyl, C$_3$–C$_7$ cycloalkyl, or, alternately, R$^1$ and R$^2$ can be taken together with the carbon to which they are attached to form a 3–7 membered saturated carbocyclic ring system or can be taken together to be keto;

R$^{5B}$, R$^{6B}$ and R$^{5C}$ are independently selected from C$_1$–C$_6$ alkyl or aryl; and step (7) is carried out in the presence of a suitable acid catalyst.

7. A process of claim 3 wherein R$^{5B}$, R$^{6B}$ and R$^{5C}$ are independently selected from C$_1$–C$_3$ alkyl.

8. A process of claim 1 wherein:
R$^{42}$=R$^{43}$ and R$^{5A}$=R$^{6A}$.

9. A process of claim 1 wherein the hydroxy protecting groups R$^{5A}$ and R$^{6A}$ are selected from: triethylsilyl, tetrahydropyranyl, dimethyl isopropylsilyl, trimethylsilyl, or t-butyldimethylsilyl.

10. A process of claim 1 wherein: the suitable hydroxy protecting group reagent in step (3) is a halogen activated triethylsilyl hydroxy protecting group reagent; step (3) is carried out in the presence of a base; R$^{5A}$ and R$^{6A}$ are triethylsilyl; and the reagent or conditions to effect the removal of the R$^{5A}$ and R$^{6A}$ hydroxy protecting groups in step (6) comprises carrying out the reaction in the presence of an acid.

11. A process of claim 1 wherein the amine protecting groups R$^{42}$ and R$^{43}$ are selected from:

benzyloxycarbonyl; 1-(p-biphenyl)-1-methylethoxycarbonyl;

9-fluorenylmethyloxycarbonyl;

tert-butyloxycarbonyl; ethoxycarbonyl;

diisopropylmethoxycarbonyl; allyloxycarbonyl; 2,7-di-t-butyl-(10,10-dioxo-10,10,10,10-tetrahydrothio-xanthyl)]methyloxycarbonyl;

2-trimethylsilylethyloxycarbonyl;

2-phenylethyloxycarbonyl; 1,1-dimethyl-2,2-dibromoethyloxycarbonyl;

1-methyl-1-(4biphenylyl)ethyloxycarbonyl;

p-nitrobenzyloxycarbonyl; 2-(ptoluenesulfonyl)ethyloxycarbonyl;

m-chloro-pacyloxybenzyloxycarbonyl;

5-benzylsoxazolylmethyloxycarbonyl;

p-(dihydroxyboryl)benzyloxycarbonyl;

m-nitrophenyloxycarbonyl; o-nitrobenzyloxycarbonyl;

3,5-dimethoxybenzyloxycarbonyl; 3,4-dimethoxy-6-nitrobenzyloxycarbonyl;

N'-p-toluenesulfonylaminocarbonyl;

t-amyloxycarbonyl; p-decyloxybenzyloxycarbonyl;

diisopropylmethoxycarbonyl; 2,2-dimethoxycarbonylvinyloxycarbonyl;

di(2-pyridyl)methyloxycarbonyl;

2-furanylmethyloxycarbonyl.

12. A process of claim 1 wherein the solvent in step (1) and step (2) is dichloromethane.

13. A process of claim 1 wherein each of the intermediate compounds of formula (II) to (VIII) are carried through to the next step in the process without chromatographic isolation prior to the next step.

14. A process of claim 1 wherein the α,α'-tetraalkyl N-oxide free radical is 2,2,6,6-tetramethyl-1-piperidinyloxy free radical.

15. A process for preparing a compound of formula (II):

wherein:

R$^{42}$ is an amine protecting group which is stable to base, oxidation, and (V$_2$Cl$_3$(THF)$_6$)$_2$(Zn$_2$Cl$_6$), and which can be removed using a reagent or conditions, or combination thereof, which will not effect removal of triethylsilyl hydroxyl protecting group;

R$^4$ is selected from the following groups:
hydrogen;
C$_1$–C$_8$ alkyl substituted with 0–3 R$^{11}$;
C$_2$–C$_8$ alkenyl substituted with 0–3 R$^{11}$;
C$_2$–C$_8$ alkynyl substituted with 0–3 R$^{11}$;

R$^{4A}$ and R$^{7A}$ are H;

R$^{11}$ is selected from one or more of the following:
H, cyano, —CH$_2$NR$^{13}$R$^{14}$, —NR$^{13}$R$^{14}$, —OR$^{13}$, —(O)$_m$R$^{13}$, C$_1$–C$_4$ alkyl, C$_2$–C$_4$ alkenyl, C$_3$–C$_{10}$ cycloalkyl substituted with 0–2 R$^{12}$, a C$_5$–C$_{14}$ carbocyclic residue substituted with 0–3 R$^{12}$, aryl(C$_1$–C$_3$ alkyl)—, substituted with 0–2 R$^{12}$, or aryl substituted with 0–3 R$^{12}$;

R$^{12}$, when a substituent on carbon, is selected from one or more of the following:
phenyl, benzyl, phenethyl, phenoxy, benzyloxy, O-protected hydroxy, cyano, C$_1$–C$_4$ alkyl, C$_3$–C$_6$ cycloalkyl, C$_3$–C$_6$ cycloalkylmethyl, C$_7$–C$_{10}$ arylalkyl, C$_1$–C$_4$ alkoxy, sulfonamide, C$_3$–C$_6$ cycloalkoxy, —OR$^{13}$, C$_1$–C$_4$ alkyl substituted with —NR$^{13}$R$^{14}$, —NR$^{13}$R$^{14}$, C$_2$–C$_6$ alkoxyalkylene optionally substituted with —Si(CH$_3$)$_3$, C$_1$–C$_4$ benzyloxyalkyl, methylenedioxy, ethylenedioxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —S(O)$_m$R$^{13}$, —SO$_2$NR$^{13}$R$^{14}$, —NHSO$_2$R$^{14}$, 2-(1-morpholino)ethoxy, or —C(R$^{14}$)=N(OR$^{14}$); or R$^{12}$ may be a 3- or 4- carbon chain attached to adjacent carbons on the ring to form a fused 5- or 6-membered ring, said 5- or 6- membered ring being optionally substituted on the aliphatic carbons with C$_1$–C$_4$ alkyl, C$_1$–C$_4$ alkoxy, O-protected hydroxy, or —NR$^{13}$R$^{14}$; or, when R$^{12}$ is attached to a saturated carbon atom, it may be =O or =S; or when R$^{12}$ is attached to sulfur it may be =O;

R$^{12}$, when a substituent on nitrogen, is selected from one or more of the following:
phenyl, benzyl, phenethyl, benzyloxy, C$_1$–C$_4$ benzyloxyalkyl, C$_1$–C$_4$ alkoxy, C$_1$–C$_4$ alkyl, C$_3$–C$_6$ cycloalkyl, C$_3$–C$_6$ cycloalkylmethyl, —CH$_2$NR$^{13}$R$^{14}$, —NR$^{13}$R$^{14}$, C$_2$–C$_6$ alkoxyalkyl C$_1$–C$_4$ alkylcarbonyl, —C(R$^{14}$)=N(OR$^{14}$);

R$^{13}$ is C$_1$–C$_6$ alkyl; C$_3$–C$_6$ alkoxyalkyl; C$_2$–C$_4$ alkenyl; phenyl; or benzyl;

R$^{14}$ is benzyloxy, C$_1$–C$_6$ alkyl, C$_1$–C$_6$ alkoxy, C$_2$–C$_6$ alkenyl, phenyl, benzyl, an amine protecting group when R$^{14}$ is bonded to N, or a hydroxy protecting group when R$^{14}$ is bonded to 0;

m is 0, 1 or 2;

comprising:

(a) contacting a compound of formula (I):

with 2,2,6,6-tetramethyl-1-piperidinyloxy free radical, sodium hypochlorite, and sodium bromide, in water and a suitable aprotic solvent, to form a compound of the formula (II);

wherein:
sodium hypochlorite is present at a concentration of 0.35 to 0.55M; and
sodium bromide is present in a molar equivalent ratio of 0.4 to 0.9 equivalents of sodium bromide per equivalent of the compound of formula (I); and, (b) quenching, with sodium thiosulfate, any oxidants present in the solution formed from step (a) prior to separation of the aprotic solvent and water phases.

16. A process of claim 15 wherein: sodium hypochlorite is present at a concentration of 0.42 to 0.49M; and sodium bromide is present in a molar equivalent ratio of 0.5 equivalents of sodium bromide per equivalent of the compound of formula (I).

17. The process of claim 15, wherein said aprotic solvent is methylene chloride.

18. The process of claim 16, wherein said aprotic solvent is methylene chloride.

19. A process for preparing a compound of formula (II):

wherein:

$R^{42}$ is an amine protecting group which is stable to base, oxidation, and $(V_2Cl_3(THF)_6)_2(Zn_2Cl_6)$, and which can be removed using a reagent or conditions, or combination thereof, which will not effect removal of triethylsilyl hydroxyl protecting group;

$R^4$ is selected from the following groups:
hydrogen;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;

$R^{4A}$ and $R^{7A}$ are H;

$R^{11}$ is selected from one or more of the following:
H, cyano, —$CH_2NR^{13}R^{14}$, —$NR^{13}R^{14}$, —$OR^{13}$— $S(O)_mR^{13}$, $C_1$–$C_4$ alkyl, $C_2$–$C_4$ alkenyl, $C_3$–$C_{10}$ cycloalkyl substituted with 0–2 $R^{12}$ a $C_5$–$C_{14}$ carbocyclic residue substituted with 0–3 $R^{12}$, aryl($C_1$–$C_3$ alkyl)—, substituted with 0–2 $R^{12}$, or aryl substituted with 0–3 $R^{12}$;

$R^{12}$, when a substituent on carbon, is selected from one or more of the following:
phenyl, benzyl, phenethyl, phenoxy, benzyloxy, O-protected hydroxy, cyano, $C_1$–$C_4$ alkyl, $C_3$–$C_6$ cycloalkyl, $C_3$–$C_6$ cycloalkylmethyl, $C_7$–$C_{10}$ aralkyl, $C_1$–$C_4$ alkoxy, sulfonamide, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene optionally substituted with —$Si(CH_3)_3$, $C_1$–$C_4$ benzyloxyalkyl, methylenedioxy, ethylenedioxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, 2-(1-morpholino)ethoxy, or —$C(R^{14})=N(OR^{14})$;

or $R^{12}$ may be a 3- or 4- carbon chain attached to adjacent carbons on the ring to form a fused 5- or 6-membered ring, said 5- or 6- membered ring being optionally substituted on the aliphatic carbons with $C_1$–$C_4$ alkyl, $C_1$–$C_4$ alkoxy, O-protected hydroxy, or —$NR^{13}R^{14}$; or, when $R^{12}$ is attached to a saturated carbon atom, it may be =O or =S; or when $R^{12}$ is attached to sulfur it may be =O;

$R^{12}$, when a substituent on nitrogen, is selected from one or more of the following:
phenyl, benzyl, phenethyl, benzyloxy, $C_1$–$C_4$ benzyloxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkylcarbonyl, —$C(R^{14})=N(OR^{14})$;

$R^{13}$ is $C_1$–$C_6$ alkyl; $C_3$–$C_6$ alkoxyalkyl; $C_2$–$C_4$ alkenyl; phenyl; or benzyl;

$R^{14}$ is benzyloxy, $C_1$–$C_6$ alkyl, $C_1$–$C_6$ alkoxy, $C_2$–$C_6$ alkenyl, phenyl, benzyl, an amine protecting group when $R^{14}$ is bonded to N, or a hydroxy protecting group when $R^{14}$ is bonded to O;

m is 0, 1 or 2;

comprising:

(a) contacting a compound of formula (I):

with 2,2,6,6-tetramethyl-1-piperidinyloxy free radical, sodium hypochlorite, and sodium bromide, in water and a suitable aprotic solvent, to form a compound of the formula (II);

wherein:
sodium hypochlorite is present at a concentration of 0.35 to 0.55M; and,
sodium bromide is present in a molar equivalent ratio of at least about 0.4 equivalents of sodium bromide per equivalent of the compound of formula (I); and, (b) quenching, with sodium thiosulfate, any oxidants present in the solution formed from step (a) prior to separation of the aprotic solvent and water phases.

20. The process of claim 19, wherein said aprotic solvent is methylene chloride.

* * * * *

UNITED STATES PATENT AND TRADEMARK OFFICE
CERTIFICATE OF CORRECTION

PATENT NO. : 5,530,124
DATED : June 25, 1996
INVENTOR(S) : Lillian A. Radesca, et. al.

It is certified that error appears in the above-indentified patent and that said Letters Patent is hereby corrected as shown below:

At column 43, line 19, delete the "." and insert -- ; wherein said process is conducted on multikilogram scale. --

At column 44, line 54, delete the "." and insert -- ; wherein said process is conducted on multikilogram scale. --

Signed and Sealed this

Twenty-ninth Day of July, 1997

Attest:

BRUCE LEHMAN

*Attesting Officer*  *Commissioner of Patents and Trademarks*